United States Patent
Kleinberg et al.

(10) Patent No.: US 9,370,476 B2
(45) Date of Patent: Jun. 21, 2016

(54) **COMPOSITIONS AND METHODS FOR ALTERING HUMAN CUTANEOUS MICROBIOME TO INCREASE GROWTH OF *STAPHYLOCOCCUS EPIDERMIDIS* AND REDUCE *STAPHYLOCOCCUS AUREUS* PROLIFERATION**

(71) Applicant: The Research Foundation for The State University of New York, Albany, NY (US)

(72) Inventors: Israel Kleinberg, Smithtown, NY (US); Zegong Zhang, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/869,802

(22) Filed: Sep. 29, 2015

(65) Prior Publication Data

US 2016/0089395 A1 Mar. 31, 2016

Related U.S. Application Data

(60) Provisional application No. 62/057,040, filed on Sep. 29, 2014, provisional application No. 62/116,082, filed on Feb. 13, 2015.

(51) Int. Cl.
| | |
|---|---|
| *A61K 8/44* | (2006.01) |
| *A61Q 15/00* | (2006.01) |
| *A61K 8/27* | (2006.01) |
| *A61K 9/00* | (2006.01) |
| *A61K 31/198* | (2006.01) |
| *A61K 33/30* | (2006.01) |

(52) U.S. Cl.
CPC ... *A61K 8/44* (2013.01); *A61K 8/27* (2013.01); *A61K 9/0014* (2013.01); *A61K 31/198* (2013.01); *A61K 33/30* (2013.01); *A61Q 15/00* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,089,942 A | 5/1978 | Boré et al. | |
| 4,565,693 A | 1/1986 | Marschner | |

(Continued)

FOREIGN PATENT DOCUMENTS

| | | |
|---|---|---|
| WO | 2009/100281 | 8/2009 |
| WO | 2011/073440 | 6/2011 |

(Continued)

OTHER PUBLICATIONS

International Search Report and Written Opinion for International Application No. PCT/US2015/053015 dated Dec. 14, 2015.

(Continued)

*Primary Examiner* — Robert A Wax
*Assistant Examiner* — Melissa Mercier
(74) *Attorney, Agent, or Firm* — Fish & Richardson P.C.

(57) ABSTRACT

A composition including arginine or a salt thereof, a zinc salt, preferably arginine bicarbonate and zinc carbonate (ABZC), in combination, plus one or more physiologically acceptable excipients, administered for the modification of cutaneous microfloras, generally to inhibit the growth of pathogenic *Staphylococcus aureus* bacteria and also promote the growth of non-pathogenic *Staphylococcus epidermidis* bacteria, and methods for using such composition.

16 Claims, 23 Drawing Sheets

(56) References Cited

U.S. PATENT DOCUMENTS

| | | | |
|---|---|---|---|
| 4,634,588 | A | 1/1987 | Moroe |
| 4,708,863 | A | 11/1987 | Bews et al. |
| 5,696,169 | A | 12/1997 | Otsu et al. |
| 5,824,663 | A | 10/1998 | Brockett et al. |
| 8,557,228 | B2 | 10/2013 | Fitzgerald et al. |
| 2010/0322986 | A1* | 12/2010 | Prencipe ................ A61K 8/02 424/401 |
| 2011/0033409 | A1 | 2/2011 | Tanaka et al. |
| 2013/0331384 | A1 | 12/2013 | Gallo et al. |

FOREIGN PATENT DOCUMENTS

| | | | |
|---|---|---|---|
| WO | 2014/098813 | 6/2014 | |
| WO | WO 2015094254 A1 * | 6/2015 | ............. A61K 8/27 |

OTHER PUBLICATIONS

Bauer et al., "Antibiotic Susceptibility Testing by a Standardized Single Disk Method", The American Journal of Clinical Pathology, 45(4):493-496 (1966).

Chen et al., "Evolving Epidemiology of Pediatric *Staphylococcus aureus* Cutaneous Infections in a Baltimore Hospital", Pediatric Emergency Care, Lippincott Williams & Wilkins, 22(10):717-723 (2006).

David and Daum, "Community-Associated Methicillin-Resistant *Staphylococcus aureus*: Epidemiology and Clinical Consequences of an Emerging Epidemic", Clin. Microb. Reviews p. 616-687 (2010).

Denepitiya and Kleinberg, "A Comparison of the Acid-Base and Aciduric Properties of Various Serotypes of the Bacterium *Streptococcus mutans* Associated with Dental Plaque", Archs Oral Biol. 29(5):385-393 (1984).

Denepitiya and Kleinberg, "A Comparison of the Microbial Compositions of Pooled Human Dental Plaque and Salivary Sediment", Archs oral Biol. (27):739-745 (1982).

Emter and Natsch, "The Sequential Action of a Dipeptidase and a β-Lyase Is Required for the Release of the Human Body Odorant 3-Methyl-3-sulfanylhexan-1-ol from a Secreted Cys-Gly-(S) Conjugate by *Corynebacteria*", J. of Biol. Chem. 283(30):20645-20655 (2008).

Frank et al., "The Human Nasal Microbiota and *Staphylocccus aureus* Carriage", PLoS ONE, www.plosone.org; 5(5):e10598 (2010).

French, "Methods for screening for methicillin-resistant *Staphylocccus aureus* carriage", The Author, Journal Compilation © The Author European Society of Clinical Microbiology and Infectious Diseases, 15(Suppl7): 10-16 (2009).

Han et al., "Evaluation of mannitol sugar agar, CHROMagar Staph aureus and CHROMagar MRSA for detection of methicillin-resistant *Staphylocccus aureus* from nasal swab specimens", J. of Medical Microbiology, 56:43-46 (2007).

Jackman, "Body Odor—The Role of Skin Bacteria", Seminars in Dermatology 1(2):143-148 (1982).

Kleinberg and Codipilly. "Modeling of the oral malodor system and methods of analysis", Quinlessence International, 30:357-369 (1999).

Kleinberg and Codipilly, "Cysteine challenge testing:a powerful tool for examining oral malodour processes and treatments in vivo", International Dental Journal 52:221-228 (2002).

Kleinberg and Codipilly, "$H_2S$ generation and $E_h$ reduction in cysteine challenge testing as a means of determining the potential of test products and treatments for inhibiting oral malodor", J. Breath Res. 2: 1-9 (2008).

Klevens et al., "Invasive Methicillin-Resistant *Staphylococcus aureus* Infections in the Unites States", JAMA 298(15):1763-1771 (2007).

Leyden et al., "The Microbiology of the Human Axilla and Its Relationship to Axillary Odor, The Journal of Investigative Dermatology" 77:413-416 (1981).

Leyden and McGinley, "Coryneform bacteria", p. 102-115 (1993).

Mainous et al., "Nasal Carriage of *Staphylococcus aureus* and Methicillin-Resistant *S aureus* in the United States, 2001-2002", Ann. Fam. Med. 4:132-137 (2006).

Nakatsuji et al., "Skin commensal bacteria acts as antimicrobial shield: Identification of . . . *Staphylococcus epidermis*", Immunology 2: Innate Immunity & Microbiology /Abstracts; Abstract # 642 (2012).

Noble, "*Staphylococci* on the skin", The Skin of Microfolora and Microbial Skin Disease, Cambridge University Press, p. 135-152 (1993).

Pader, Oral Hygiene products and practice/ Health Sciences Library Book Collection, New York: Dekker (1988).

Peacock et al., "What determines nasal carriage of *Staphylococcus aureus*?", Trends in Microbiology 9(12):605-610 (2001).

Public Health Dispatch: Outbreaks of Community-Associated Methicillin Resistant *Staphylococcus aureus* Skin Infections—Los Angeles County, California, 2002-2003; http://www.cdc.gov/mmwr/preview/mmwrhtml/mm5205a4.htm Oct. 5, 2015.

Sandham and Kleinberg, "Effect of Glucose Concentration on Carbon Dioxide Production in a Human Salivary Sediment System", Archs oral Biol., 15:1285-1301 (1970).

Shehadeh et al., The Bacteria Responsible for Axillary Odor, II, J. Invest. Dermatol. 41:3-3 (1963).

Starkenmann et al., "Identification of the Precursor of (S)-3-Methyl-3-sulfanylhexan-1-ol, the Sulfury Malodour of Human Axilla Sweat", Chemistry and Biodiversity 2:705-716 (2005).

Taylor et al., "Characterization of the microflora of the human axilla", International Journal of Cosmetic Science 25:137-145 (2003).

Trocazz et al., "3-Methyl-3-sulfanylhexan-1-ol as a Major Descriptor for the Human Axilla-Sweat Odour Profile", Chemistry & Biodiversity 1:1022-1035 (2004).

Uehara et al, "Bacterial Interference among nasal inhabitants: eradication of *Staphylococcus aureus* from nasal cavities by artificial implantation of *Corynebacterium* sp.", J. of Hospital Infection 44:127-133 (2000).

Wertheim et al., "The role of nasal carriage in *Staphylococcus aureus* infections", The Lancet Infectious Diseases, 5:751-762 (2005).

Wueyeweera and Kleinberg, "Acid-Base pH Curves in Vitro with Mixtures of Pure Cultures of Human Oral Microorganisms", Archs oral Biol. 34(1):55-64 (1989).

Zeng et al., "Analysis of Characteristic Odors From Human Male Axillae", J. of Chem. Ecology 17(7):1469-1493 (1991).

* cited by examiner

COMPOSITIONS AND METHODS FOR ALTERING HUMAN CUTANEOUS MICROBIOME TO INCREASE GROWTH OF *STAPHYLOCOCCUS EPIDERMIDIS* AND REDUCE *STAPHYLOCOCCUS AUREUS* PROLIFERATION

FIELD OF THE INVENTION

The present invention relates to compositions and methods for selectively increasing the growth of *Staphylococcus epidermidis* and inhibiting the growth of *Staphylococcus aureus* bacteria in the cutaneous microbiome. More particularly, the present invention relates to compositions and methods for increasing the growth of *Staphylococcus epidermidis* and reducing the incidence of MRSA and MSSA by the selective inhibition of *Staphylococcus aureus*.

BACKGROUND OF THE INVENTION

The cutaneous microbiome in humans is comprised of a variety of microorganisms, of which staphylococci, corynebacteria and propionibacteria are among the most prominent (Starkemann et al., 2005, Troccaz et al., 2004, Jackman, 1982). These bacteria act upon odorless precursors contained in sweat per se, producing sugars, sugar amines, amino acids, and short chain carboxylic acids (SCCAs), of which some are degraded further to products that include odorants that are associated to a major extent with cutaneous odor (Zeng et al, 1991; Jackman, 1982).

One frequent undesirable member of the cutaneous microbiome, *Staphylococcus aureus* (*Staph. aureus*, including methicillin-resistant *Staph. aureus* (MRSA) and methicillin-susceptible *Staph. aureus* (MSSA)), has a well-known role in invasive infections in humans. It is one of the most problematic of human pathogens, because it is capable of wide infection and fatalities (see, e.g., David et al., 2010, Mainous III et al., 2006, Klevens et al., 2007). Antibiotics used against it have achieved limited success. Methicillin is effective but limited because of adaptation, which can result in the emergence of MRSA, which is representative of antibiotic failure occurring now more so with increasing frequency of use (see, e.g., David et al 2010, Chen et al 2006, Centers for Disease Control and Prevention 2003).

SUMMARY OF THE INVENTION

The present invention is directed to compositions of zinc salts and arginine and/or its salts for the selective inhibition of *Staph. aureus* growth and the favoring of the growth of *Staph. epidermidis*, and methods for using such compositions.

The present invention is directed to topical cutaneous compositions including arginine or a salt thereof, a zinc salt, and, optionally, a buffer for maintaining the pH of the composition at 6.0 or greater, and methods for using such compositions. The compositions and methods of the invention are useful in selectively inhibiting the growth of *Staphylococcus aureus* and increasing the growth of *Staphylococcus epidermidis* bacteria in the cutaneous microbiome.

BRIEF DESCRIPTION OF THE DRAWINGS

The invention will be more fully understood from the following detailed description taken in conjunction with the accompanying figures, in which.

DETAILED DESCRIPTION OF THE INVENTION

Figure 1:
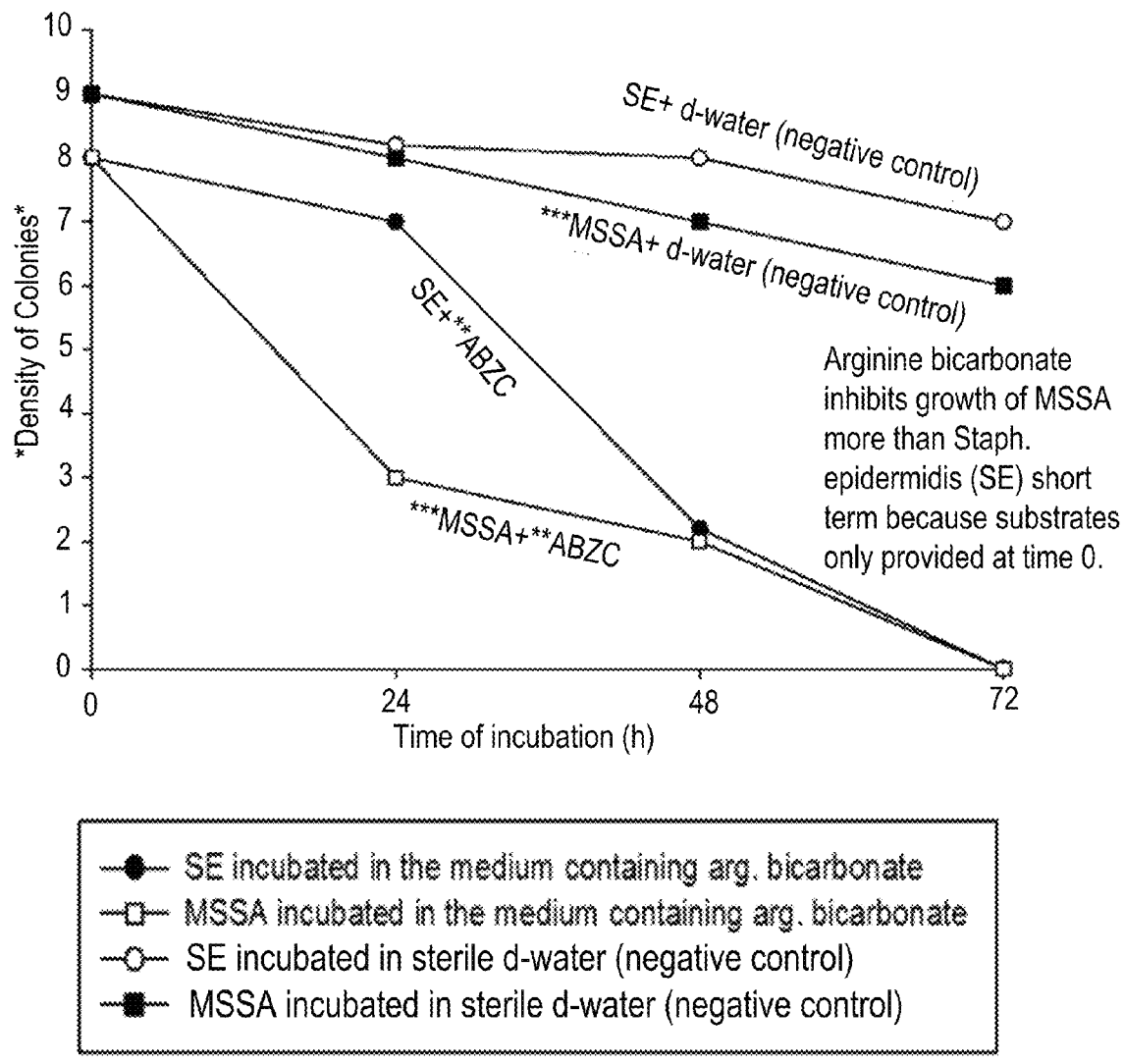
FIG. 1 is a graph showing the effect of arginine bicarbonate on the growth of 8.3% (v/v) *Staphylococcus epidermidis* and *Staphylococcus aureus* (MSSA) incubated with 12.0 mM zinc carbonate, 6.0 mM CIL and 24.0 mM arginine bicarbonate at 37° C. for 72 hours.

Corynebacteria, staphylococci and proprionibacteria are among the main microorganisms present in the cutaneous microbiome, with Staph. epidermidis, C. striatum and P. avidum as prominent representative bacteria Unexpectedly, it has been discovered that certain compositions including a zinc salt and arginine and/or its salt are useful as compositions for modifying cutaneous microflora, inhibiting Staph. aureus growth while favoring Staph. epidermidis growth. This ability to select between Staph. aureus and Staph. epidermidis allows the treatment of significant physiological and health-related disease conditions caused by aberrant or excessive growth of Staph. aureus (see, e.g., Peacock et al., 2001, Uehara et al., 2000). Although Staph. aureus is capable of wide infection and fatalities (see, e.g., David et al., 2010, Mainous III et al., 2006, Klevens et al., 2007), current antibiotic treatments have achieved limited success due to the emergence of resistant Staph. aureus strains, e.g., MRSA (see, e.g., David et al 2010, Chen et al 2006, Centers for Disease Control and Prevention 2003). A recent discovery has shown that firmicidin (Gallo et al., 2013, Nakatsuji et al., 2012), a newly discovered antibiotic generated by Staph. epidermidis, can reduce Staph. aureus, but it is not known whether this will, like other antibiotics, succumb to adaptation and loss of effectiveness. From a commercial standpoint, this approach is likely to be costly.

Unlike traditional antibacterial treatments, the compositions of the present invention are aimed at modulating natural interactions between Staph. aureus and other prominent members of the cutaneous microflora, e.g., Staph. epidermidis (see, e.g., Frank et al., 2010, Uehara et al., 2000, Wertheim et al., 2005). These bacteria naturally compete, e.g., for local resources and attachment to mucosal sites (Frank et al., 2010). The compositions of the invention, rather than merely targeting Staph. aureus, render an ecological change that favors selection of desirable Staph. epidermidis over non-desirable Staph. aureus bacteria.

The compositions of the present invention target Staph. aureus directly, and also enhance the ability of other, non-pathogenic bacteria (e.g., Staph. epidermidis) to out-compete Staph. aureus. The compositions disclosed here are less likely to be susceptible to the emergence of resistant strains (e.g., MRSA) than traditional antibacterial treatments.

A further advantage of the present invention is that the compositions disclosed herein are effective in reducing cutaneous odor production. Thus, a single topical composition may be used as both deodorant and for modification of the cutaneous microflora.

Compositions as described herein are administered, preferably topically, Dosage forms are solid or free-flowing. Dosage forms include, but are not limited to, soaps, sprays, drops, aerosols, powders, roll-ons, lotions, creams, sticks, solutions, sachets, colloidal suspensions, films, patches and ointments.

The compositions as described herein may have a pH of at least 6.0, or at least 7.0, or at least 8.0, or at least 9.0 upon topical administration.

The compositions as described herein may optionally include one or more physiologically acceptable buffers sufficient to maintain the pH of said composition, e.g., at 6.0 or greater, at 7.0 or greater, at 8.0 or greater, or at 9.0 or greater upon topical application. Such buffers are generally known in the art, and may include, e.g., ACES, acetic acid, ADA, AMP, AMPD, bicine, bis-Tris, bis-Tris propane, BES, boric acid, cacodylate, CABS, CAPS, CAPSO, CHES, citric acid, diethanolamine, DIPSO, EPPS/HEPPS, ethanolamine, formic acid, glycine, glycylglycine, HEPES, HEPPSO, histidine, imidazole, lactic acid, maleic acid, malic acid, MES, MOPS, MOPSO, morpholine, phosphate, phosphoric acid, picolinic acid, PIPES, piperazine, piperidine, pivalic acid, POPSO, pyridine, succinic acid, TAPS, TAPSO, TEA, TES, tricine, and/or Tris.

Except where otherwise noted, the terms "axillary odor" and "foot odor" are used interchangeably herein, the terms "microbiome," "microbiota," and "microflora" are used interchangeably herein, the terms "foot," "foot web," "foot-web," "toe," "toe web" and "toe-web" are used interchangeably herein, and the terms "odor" and "malodor" are used interchangeably herein.

The terms "cutaneous" and "skin" refer, in the context of the present invention, regions of the human body including, e.g., the axilla, foot-webs and nasal atrium.

The terms "physiologically acceptable" and "physiologically-acceptable" denote, in the context of the present invention, "safe and effective when administered to humans and/or mammals in need thereof," e.g., to reduce axillary odor, promote the growth of *Staphylococcus epidermidis* bacteria, inhibit the growth of *Staphylococcus aureus* bacteria, or any or all of the preceding.

EXAMPLES

The following examples are intended to illustrate, but not limit, the present disclosure.
Growth of *Staph. aureus* (MSSA or MRSA) and *Staph. epidermidis* when one or the other or a mixture of the two bacteria were incubated in the presence of (i) cysteine and (ii) isoleucine, leucine, phenylalanine. Zinc carbonate was also provided with and without arginine bicarbonate at 37° C. for 72 hours and with additional above ingredients adding into the cultural media in 37° C. water bath in 24 and 48 hours.
Materials and Methods for Growth Comparison Experiments between *Staph. epidermidis* and *Staph. aureus*
(a) Preparation of Agar plates containing various bacterial growth media. Preparation included (i) BHI Blood agar (Fisher Scientific, Springfield, N.J. USA) and (ii) CHROMagar *Staph. aureus* agar (CHROMagar, Paris, France), especially prepared for the isolation and identification of *Staph. aureus*; if present, it results in colonies that show a characteristic mauve color that enables ease of identification (French, 2009, Han et al., 2007).
(b) Stock solutions of CIL amino acids. These amino acids include cysteine, isoleucine and leucine with each present at a concentration of 72 mM. Aqueous solutions of each were sterilized by syringe filtering.
(c) Stock aqueous solutions of arginine bicarbonate at 144 mM and zinc carbonate at 72 mM. Stock solutions of 144 mM arginine bicarbonate were sterilized together with 72 mM zinc carbonate by syringe filtering. Zinc carbonate has a limited solubility and hence is sterilized by first autoclaving as a powder and then dissolving it until saturation in sterile distilled water is achieved. This means that at 72 mM and above, it may have to be used as a zinc carbonate suspension.
(d) Rabbit coagulase plasma (PL 850) and Prolex Staph Xtra Latex kits (PL.1080). Both of these items are provided as a kit and are obtained from Pro-Lab Diagnostics, Austin, Tex. They are prepared for the identification of pathogenic staphylococci (e.g., *Staph. aureus*).
(e) Experimental and control incubation mixtures containing *Staph. epidermidis* (ATCC 12228) and *Staph. aureus* (MSSA and/or MRSA). These incubation mixtures were prepared for comparison purposes and included MSSA (ATCC 25923) or MRSA (ATCC 33591) bacterial species mixed with the microorganism *Staph. epidermidis*. Pure cultures of *Staph. epidermidis* and *Staph. aureus* (MSSA or MRSA) were each prepared as 25% (v/v) bacterial suspensions in sterile distilled water. As above and as much as possible, bacterial pellets were broken up into fine particles, by stirring with a sterile TB syringe and a 25-27 gauge needle, if and when needed.

As a preparatory step, the resulting suspensions obtained were incubated in a shaking water bath at 37° C. for one hour, in order to deplete stored substrates acquired by some bacteria, during their preparatory growth period (Wijeyeweera and Kleinberg, 1989). The pH of each of the above bacterial suspensions was then measured by transferring 0.25 ml of such to a small sterile test-tube and measuring its pH. This made it easier to avoid any bacterial contamination during handling. Samples were then stored at 4° C. until time of inoculation of agar plates.
Preparation of Experimental and Control Samples Preparation was performed according to information in Table 1 below.

TABLE 1.1

Experimental (A and B) and negative control (C) samples were prepared according to the following ABC Composition Tables:

A.

| Composition | | Experimental samples (ml) | | | | | | Final concentrations | | |
|---|---|---|---|---|---|---|---|---|---|---|
| | | I | II | III | IV | V | VI | | | |
| Amino acids | Cys 72 mM | 0.225 | 0.225 | 0.225 | 0.225 | 0.225 | 0.225 | 6 mM | | |
| | Ieu 72 mM | 0.225 | 0.225 | 0.225 | 0.225 | 0.225 | 0.225 | 6 mM | | |
| | Ileu 72 mM | 0.225 | 0.225 | 0.225 | 0.225 | 0.225 | 0.225 | 6 mM | | |
| Zinc Carbonate (72 mM) | | 0.45 | 0.45 | 0.45 | 0.45 | 0.45 | 0.45 | 12 mM | | |
| Arg. Bicarbonate (144 mM) | | 0.45 | 0.45 | 0.45 | — | — | — | 24 mM (IV, V, VI = 0 mM) | | |
| *Staph. epidermidis* (25%) | | 0.45 | — | 0.90 | 0.45 | — | 0.90 | 8.3% | mixture | 4.15% |
| *Staph. aureus* 25% (MSSA or MRSA) | | 0.45 | 0.90 | — | 0.45 | 0.90 | — | 8.3% | | 4.15% |
| D-water | | 0.225 | 0.225 | 0.225 | 0.675 | 0.675 | 0.675 | | | |
| Total volume (ml) | | 2.70 | 2.70 | 2.70 | 2.70 | 2.70 | 2.70 | | | |

TABLE 1.1-continued

Experimental (A and B) and negative control (C) samples were prepared according to the following ABC Composition Tables:

B.

| Composition | | Experimental samples (ml) | | | | | | Final concentrations | | |
|---|---|---|---|---|---|---|---|---|---|---|
| | | IA | IIA | IIIA | IB | IIB | IIIB | | | |
| Amino acids | Cys 72 mM | 0.225 | 0.225 | 0.225 | 0.225 | 0.225 | 0.225 | | 6 mM | |
| | Ieu 72 mM | 0.225 | 0.225 | 0.225 | 0.225 | 0.225 | 0.225 | | 6 mM | |
| | Ileu 72 mM | 0.225 | 0.225 | 0.225 | 0.225 | 0.225 | 0.225 | | 6 mM | |
| Zinc Carbonate (72 mM) | | 0.45 | 0.45 | 0.45 | 0.45 | 0.45 | 0.45 | | 12 mM | |
| Arg. Bicarbonate (44 mM) | | 0.45 | 0.45 | 0.45 | 0.45 | 0.45 | 0.45 | | 24 mM | |
| *Staph. epidermidis* (25%) | | 0.45 | — | 0.90 | 0.45 | — | 0.90 | 8.3% | mixture | 4.15% |
| *Staph. aureus* 25% (MRSA) | | 0.45 | 0.90 | — | 0.45 | 0.90 | — | 8.3% | | 4.15% |
| D-water | | 0.225 | 0.225 | 0.225 | 0.225 | 0.225 | 0.225 | | | |
| Total volume (ml) | | 2.70 | 2.70 | 2.70 | 2.70 | 2.70 | 2.70 | | | |

C.

| Composition | | Negative controls | | | Final concentrations | | |
|---|---|---|---|---|---|---|---|
| | | 1 | 2 | 3 | | | |
| Amino acids | Cys 72 mM | — | — | — | | — | |
| | Ieu 72 mM | — | — | — | | — | |
| | Ileu 72 mM | — | — | — | | — | |
| Zinc Carbonate (72 mM) | | — | — | — | | — | |
| Arg. Bicarbonate (144 mM) | | — | — | — | | — | |
| *Staph. epidermidis* (25%) | | 0.45 | — | 0.90 | 8.3% | mixture | 4.15% |
| *Staph. aureus* 25% (MSSA or MRSA) | | 0.45 | 0.90 | — | 8.3% | | 4.15% |
| D-water | | 1.80 | 1.80 | 1.80 | | | |
| Total volume (ml) | | 2.70 | 2.70 | 2.70 | | | |

Arginine bicarbonate is absent in IV, V and VI

Dilutions of Experimental and Negative Control Samples and Inoculations of BHI Blood Agar and CHROMagar *Staph. aureus* Plates Serial dilutions from $10^1$ to $10^{10}$ of each of experimental samples I, II, III, IV, V, VI and control samples 1, 2, 3 (see Table 1) were prepared with sterile distilled water. Each dilution contained 0.1 ml of serial diluted sample and 0.9 ml of sterile distilled water. BHI Blood agar plates were then inoculated with a mixture of 100 µl of a $10^4$ to $10^{10}$ concentration of *Staph. epidermidis* bacteria and 100 µl of a $10^4$ to $10^{10}$ sample of *Staph. aureus* (MSSA or MRSA) mixture (Samples I, IV and Negative Control 1) onto CHROMagar *Staph. aureus* plates using sterile glass bars on a turning table, respectively.

Incubation Procedures

As a first precautionary step, all agar plates were incubated for 24 hours in a 37° C. incubator and examined thereafter for bacterial growth to ensure initial agar plate sterility. Plates were then inoculated with samples taken at times 0, 24, 48 and 72 hours in succession throughout the 4 days of incubation. Successive inoculations consisted of the transfer of bacterial samples from a prior incubation to a subsequent fresh sterile plate, followed by incubation at 37° C. for 24-48 hours and subsequently repeating the process.

Colony density was scored for each of the plates as follows: between 0 and 10 as 0—no colonies; 1—<10 colonies; 2—10 to 20 colonies; 3—20 to 30 colonies; 4—30 to 50 colonies; 5—50 to 100 colonies; 6—100 to 250 colonies; 7—250 to 500 colonies; 8—>500 colonies; 9—colonies almost fused to form a layer; 10—colonies forming a bacterial layer.

Differentiation of Colonies of *Staph. aureus* and *Staph. epidermidis* Derived from Growth on BHI Blood and CHROMagar SA Plates of Samples from Incubation Mixtures with *Staph. aureus* and *Staph. epidermidis*

*Staph. aureus* colonies are usually a golden yellow color and show large and complete blood hemolytic rings around the colonies that grow on BHI Blood agar plates. Use of the coagulase serum test (test procedure of Rabbit Coagulase Plasma provided by Pro-Lab Diagnostics, Austin, Tex. USA) and Prolex Staph Xtra Latex Test (Test Protocol of Prolix™ Staph Xtra Latex Kit provided by Pro Lab Diagnostics, Austin, Tex. USA) showed positive results. On CHROMagar *Staph. aureus* plates, where *Staph. aureus* colonies readily grow, they show, as pointed out above, a mauve color. In contrast, their counterpart, *Staph. epidermidis* colonies, are white and have no or small hemolytic rings around the colonies, when grown on BHI Blood agar plates. On CHROMagar *Staph. aureus* plates, *Staph. epidermidis* is unable to grow or able to form tiny white colonies. Coagulase serum and Prolex Staph Xtra Latex testing proved negative (i.e. no coagulation).

Inoculation of Samples Incubated in a Water Bath at 37° C. for 24 Hours and then Inoculated onto (i) BHI Blood Agar Plates and (ii) CHROMagar *Staph. aureus* Plates Following the same serial dilution procedures, as done for the Day I incubation period, Samples I, II, III, IV, V, VI and 1, 2, 3 were diluted serially $10^4$ to $10^{10}$ on BHI Blood agar plates. Similarly, samples of a mixture of *Staph. epidermidis* and *Staph. aureus* (I, IV and Negative Control 1) were prepared on CHROMagar *Staph. aureus* plates and incubated using the same procedures, as were used on Day 1, i.e. incubation at 37° C. for 24-48 hours.

Addition of Extra Ingredients to Samples, IA, IIA, IIIA and IB, IIB, IIIB Incubated as on Day 1, in a Water Bath at 37° C. for 24 Hours Under aseptic conditions, samples, IA, IIA, IIIA and IB, IIB, IIIB were each centrifuged and 1.35 ml of supernatant was removed from each of samples, IA, IIA, IIIA, and 1.125 ml of supernatant from samples, IB, IIB, IIIB, respectively.

The table immediately below, lists additional ingredients introduced into samples:

TABLE 1.2

| Ingredients | Volumes (ml) added to experimental samples | | | | | |
|---|---|---|---|---|---|---|
| | IA | IIA | IIIA | IB | IIB | IIIB |
| Cys 72 mM | 0.225 | 0.225 | 0.225 | 0.225 | 0.225 | 0.225 |
| Ieu 72 mM | 0.225 | 0.225 | 0.225 | 0.225 | 0.225 | 0.225 |
| Ileu 72 mM | 0.225 | 0.225 | 0.225 | 0.225 | 0.225 | 0.225 |
| Zinc Carbonate (72 mM) | 0.225 | 0.225 | 0.225 | — | — | — |
| Arg. Bicarbonate (144 mM) | 0.450 | 0.450 | 0.450 | 0.450 | 0.450 | 0.450 |

Incubation of all experimental and control samples in a 37° C. water bath was continued for another 24 hours. Total incubation time to this point was 48 hours.

Day 3 in the Experimental Protocol (i.e., the 48-72 Hour Time Period).

This period consisted of bacterial growth on the medium agar plates inoculated on Day 2 and incubated at 37° C., (as above), on medium agar plates for another 24 hours and preparation of samples for incubation continuation for another 24 hours. Bacterial growth on BHI Blood agar and CHROMagar *Staph. aureus* plates was then determined as before.

The next step was inoculation of samples incubated in a 37° C. water bath for a total of 48 hours on the BHI Blood agar plates and CHROMagar *Staph. aureus* plates.

The same procedures of serial dilutions, as was done on Day 1, was carried out here; i.e. all samples (I, II, III, IV, V, VI, 1, 2, 3 and IA, IIA, IIIA, IB, IIB, IIIB).

Inoculated $10^4$ to $10^{10}$ serial dilutions of samples on BHI Blood agar plates and the samples of the mixture of SE and SA (I, IA, IB, IV and Negative Control 1) on CHROMagar *Staph. aureus* plates were tested by following the same procedures as was done on Day 1.

Plates were incubated as before at 37° C. between and for 24 and 48 hours.

Preparation of Samples for Incubation in a Water Bath at 37° C. for 48 Hours and Followed then for a Further 24 Hours Additional ingredients were added to samples of IA, IIA, IIIA and IB, IIB, IIIB, which were each incubated in a 37° C. water bath for a total period of 48 hours.

Samples IA, IIA, IIIA and samples IB, IIB, IIIB were centrifuged as before and 1.35 ml of supernatant was removed from samples, IA, IIA, IIIA; and 1.125 ml of supernatant was also removed from samples, IB, IIB, and IIIB, respectively.

Table 1.3, below, was followed in order to serve as a guide for adding additional ingredients into the samples:

TABLE 1.3

| Ingredients | The (ml) volumes added to the experimental samples | | | | | |
|---|---|---|---|---|---|---|
| | IA | IIA | IIIA | IB | IIB | IIIB |
| Cys 72 mM | 0.225 | 0.225 | 0.225 | 0.225 | 0.225 | 0.225 |
| Ieu 72 mM | 0.225 | 0.225 | 0.225 | 0.225 | 0.225 | 0.225 |
| Ileu 72 mM | 0.225 | 0.225 | 0.225 | 0.225 | 0.225 | 0.225 |
| Zinc Carbonate (72 mM) | 0.225 | 0.225 | 0.225 | — | — | — |
| Arg. Bicarbonate (144 mM) | 0.450 | 0.450 | 0.450 | 0.450 | 0.450 | 0.450 |

Incubation of all experimental and control samples in the water bath at 37° C. was extended for another 24 hours (i.e. 72 hours total).

Day 4 (72-96 Hours, i.e., the Last Part of the Instant Experimental Protocol)

Bacterial growth on medium agar plates inoculated on Day 3 was examined and then incubated in a water bath at 37° C. for a total of 72 hours.

Examination of Bacterial Growth on BHI Blood Agar and CHROMagar *Staph. aureus* plates inoculated on Day 3

The same methods were followed as was done on Day 4.

Inoculation of Samples Incubated at 37° C. for a Total of 72 Hours on BHI Blood Agar Plates and CHROMagar *Staph. aureus* Plates The same procedures of serial dilution were followed as was done on Day 1 for all samples (I, II, III, IV, V, VI, 1, 2, 3 and IA, IIA, IIIA, IB, IIB, IIIB).

Inoculation of $10^4$ to $10^{10}$ serial dilutions of samples on BHI Blood agar plates and the samples of the mixture of SE and SA (I, IA, IB, IV and 1) on CHROMagar *Staph. aureus* plates were the same as the procedures carried out on Day 1.

Plates were then incubated at 37° C. for 24-48 hours.

Day 5 (End of Experiment, 96 Hours Total Duration)

Examination of bacterial growth on media agar plates inoculated on Day 4 and a review of the entire experiment was performed. Examination of bacterial growth on BHI Blood agar and CHROMagar *Staph. aureus* plates inoculated was performed on Day 4 by following the same methods as was done on Day 1.

Results

Overview of the bacterial growth of all samples on the BHI Blood agar plates and on the CHROMagar *Staph. aureus* plates in the 72 hour experiments reported herein are shown in Tables 1.4, 1.5 and 1.6. FIGS. 1-15 depict the effect of different media on bacterial growth. Photographs showing colony growth data from which the Figures were derived are set forth as FIGS. 16-23.

TABLE 1.4

Density (1-10*) of colonies of *Staphylococcus epidermidis* (SE) and *Staphylococcus aureus* (MSSA) when incubated in media comprised of 6 mM cysteine, 6 mM isoleucine, 6 mM leucine (i.e., 6 mM CIL) and 12 mM zinc carbonate, with or without 24 mM arginine bicarbonate at 37° C. for 72 hours, compared with negative control (water only)

| Bacteria | Time of Incubation | Plates | Negative Control Medium (Water only) | | | | Medium-Cys, Ileu, Leu, zinc carbonate with arginine bicarbonate | | | | Medium-Cys, Ileu, Leu, zinc carbonate without arginine bicarbonate | | | |
|---|---|---|---|---|---|---|---|---|---|---|---|---|---|---|
| | | | \multicolumn{12}{c}{Times of dilution of 8.3% bacteria incubated in media} |
| | | | $10^4$ | $10^5$ | $10^6$ | $10^7$ | $10^4$ | $10^5$ | $10^6$ | $10^7$ | $10^4$ | $10^5$ | $10^6$ | $10^7$ |
| SE MSSA Mix | 0 h | BHI | 9 | 9 | 8 | 8 | 9 | 9 | 8 | 8 | 9 | 9 | 8 | 8 |
| | | Blood | 9 | 9 | 9 | 9 | 10 | 9 | 9 | 9 | 10 | 9 | 9 | 9 |
| | | Agar | 9 | 9 | 9 | 9 | 10 | 9 | 9 | 9 | 10 | 9 | 9 | 9 |
| | | CHRO | 9 | 9 | 9 | 9 | 10 | 9 | 9 | 9 | 10 | 9 | 9 | 9 |
| | | SE/SA % (~) | ... | ... | ... | ... | ... | ... | ... | ... | ... | ... | ... | ... |
| SE MSSA Mix | 24 h | BHI | 9 | 8 | 7 | 7 | 8 | 7 | 6 | 5 | 5 | 1 | 1 | 1 |
| | | Blood | 9 | 8 | 7 | 5 | 7 | 3 | 2 | 1 | 8 | 7 | 5 | 4 |
| | | Agar | 9 | 8 | 7 | 5 | 8 | 6 | 4 | 3 | 8 | 7 | 7 | 6 |
| | | CHRO | 9 | 8 | 7 | 5 | 6 | 4 | 2 | 1 | 8 | 7 | 7 | 6 |
| | | SE/SA % (~) | ... | ... | 5/95 | 10/90 | ... | 70/30 | 60/40 | 80/20 | ... | 15/85 | 15/85 | 20/80 |
| SE MSSA Mix | 48 h | BHI | 9 | 8 | 7 | 6 | 5 | 2 | 1 | 1 | 0 | 0 | 0 | 0 |
| | | Blood | 8 | 7 | 6 | 5 | 5 | 2 | 1 | 1 | 8 | 7 | 6 | 6 |
| | | Agar | 9 | 8 | 7 | 6 | 6 | 2 | 1 | 1 | 8 | 7 | 6 | 5 |
| | | CHRO | 9 | 7 | 6 | 5 | 5 | 2 | 1 | 1 | 8 | 7 | 6 | 5 |
| | | SE/SA % (~) | ... | ... | 10/90 | 20/80 | 10/90 | 15/85 | ... | ... | ... | 5/95 | 5/95 | 5/95 |
| SE MSSA Mix | 72 h | BHI | 8 | 7 | 6 | 3 | 1 | 1 | 0 | 0 | 0 | 0 | 0 | 0 |
| | | Blood | 8 | 6 | 4 | 3 | 0 | 0 | 0 | 0 | 7 | 2 | 1 | 1 |
| | | Agar | 9 | 7 | 5 | 3 | 2 | 0 | 0 | 0 | 7 | 5 | 4 | 2 |
| | | CHRO | 9 | 7 | 5 | 4 | 1 | 0 | 0 | 0 | 7 | 5 | 4 | X |
| | | SE/SA % (~) | ... | 5/95 | 5/95 | 0 | 20/80 | ... | ... | ... | ... | 0 | 0 | ... |

SE, *Staph. epidermidis*,
MSSA, *Staph. aureus* (MSSA),
Mix, mixture of *Staph. epidermidis* and *Staph. aureus* (MSSA),
CHRO, CHROMAgar medium plate selective for *Staph. aureus*, X, contamination
*Scale (0-10): 0, no colony; 1, <10; 2, 10-20; 3, 20-30; 4, 30-50; 5, 50-100; 6, 100-250; 7, 250-500; 8, >500; 9, colonies almost form a layer and are unable to count; 10, colonies form a layer

TABLE 1.5

Density (1-10*) of colonies of *Staphylococcus epidermidis* (SE) and *Staphyloccus aureus* (MRSA) when incubated in media comprised of 6 mM cysteine, 6 mM isoleucine, 6 mM leucine (i.e., 6 mM CIL) and 12 mM zinc carbonate, with or without 24 mM arginine bicarbonate at 37° C. for 72 hours, compared with negative control (water only)

| Bacteria | Time of Incubation | Plates | Negative Control Medium (Water only) | | | | Medium-Cys, Ileu, Leu, zinc carbonate with arginine bicarbonate | | | | Medium-Cys, Ileu, Leu, zinc carbonate without arginine bicarbonate | | | |
|---|---|---|---|---|---|---|---|---|---|---|---|---|---|---|
| | | | \multicolumn{12}{c}{Times of dilution of 8.3% bacteria incubated in media} |
| | | | $10^4$ | $10^5$ | $10^6$ | $10^7$ | $10^4$ | $10^5$ | $10^6$ | $10^7$ | $10^4$ | $10^5$ | $10^6$ | $10^7$ |
| SE MRSA Mix | 0 h | BHI | 9 | 9 | 8 | 7 | 9 | 8 | 8 | 8 | 9 | 8 | 8 | 8 |
| | | Blood | 10 | 9 | 8 | 8 | 10 | 9 | 8 | 8 | 9 | 8 | 8 | 8 |
| | | Agar | 10 | 9 | 8 | 7 | 10 | 9 | 8 | 8 | 9 | 8 | 8 | 8 |
| | | CHRO | 10 | 9 | 8 | 7 | 10 | 9 | 8 | 8 | 9 | 8 | 8 | 8 |
| | | SE/SA % (~) | ... | ... | ... | ... | ... | ... | ... | ... | ... | ... | ... | ... |
| SE MRSA Mix | 24 h | BHI | 9 | 9 | 8 | 8 | 8 | 8 | 8 | 8 | 7 | 6 | 6 | 6 |
| | | Blood | 10 | 9 | 9 | 8 | 7 | 5 | 5 | 5 | 9 | 8 | 8 | 8 |
| | | Agar | 10 | 9 | 8 | 8 | 8 | 7 | 5 | 5 | 9 | 8 | 8 | X |
| | | CHRO | 10 | 9 | 8 | 8 | 6 | 5 | 3 | 2 | 8 | 8 | 8 | 6 |
| | | SE/SA % (~) | ... | ... | ... | ... | ... | 60/40 | 80/20 | 80/20 | ... | ... | ... | ... |
| SE MRSA Mix | 48 h | BHI | 9 | 8 | 7 | 6 | 6 | 4 | 3 | 1-3 | 0 | 0 | 0 | 0 |
| | | Blood | 9 | 8 | 7 | 7 | 1 | 1 | 0 | 0 | 7 | 6 | 3 | 1 |
| | | Agar | 9 | 8 | 7 | 6 | 1 | 0 | 0 | 0 | 7 | 6 | 5 | 5 |
| | | CHRO | 9 | 8 | 6 | 6 | 0 | 0 | 0 | 0 | 6 | 5 | 4 | 4 |
| | | SE/SA % (~) | ... | ... | ... | 5/95 | ... | ... | ... | ... | 10/90 | 20/80 | 20/80 | 20/80 |

TABLE 1.5-continued

Density (1-10*) of colonies of *Staphylococcus epidermidis* (SE) and *Staphyloccus aureus* (MRSA) when incubated in media comprised of 6 mM cysteine, 6 mM isoleucine, 6 mM leucine (i.e., 6 mM CIL) and 12 mM zinc carbonate, with or without 24 mM arginine bicarbonate at 37° C. for 72 hours, compared with negative control (water only)

| Bacteria | Time of Incubation | Plates | Negative Control Medium (Water only) | | | | Medium-Cys, Ileu, Leu, zinc carbonate with arginine bicarbonate | | | | Medium-Cys, Ileu, Leu, zinc carbonate without arginine bicarbonate | | | |
|---|---|---|---|---|---|---|---|---|---|---|---|---|---|---|
| | | | $10^4$ | $10^5$ | $10^6$ | $10^7$ | $10^4$ | $10^5$ | $10^6$ | $10^7$ | $10^4$ | $10^5$ | $10^6$ | $10^7$ |
| SE | 72 h | BHI | 8 | 8 | 7 | 6 | 5 | 5 | 4 | 3 | 1-3 | 0 | 1-3 | 0 |
| MRSA | | Blood | 9 | 8 | 7 | 7 | 0 | 0 | 0 | 0 | 7 | 6 | 4 | 4 |
| Mix | | Agar | 8 | 8 | 7 | 6 | 1 | 1 | 1 | 1 | 7 | 7 | 6 | 6 |
| | | CHRO | 8 | 8 | 6 | 5 | 0 | 1 | 1 | 0 | 7 | 6 | 6 | 6 |
| | | SE/SA % (~) | ... | ... | ... | ... | ... | ... | ... | ... | 5/95 | 10/90 | 5/95 | 5/95 |

SE, *Staph. epidermidis*,
MRSA, *Staph. aureus* (MRSA),
Mix, mixture of *Staph. epidermidis* and *Staph. aureus* (MRSA),
CHRO, CHROMAgar medium plate selective for *Staph. aureus*, X, contamination
*Scale (0-10): 0, no colony; 1, <10; 2, 10-20; 3, 20-30; 4, 30-50; 5, 50-100; 6, 100-250; 7, 250-500; 8, >500; 9, colonies almost form a layer and are unable to count; 10, colonies form a layer

TABLE 1.6

Density (1-10*) of colonies of *Staphylococcus epidermidis* (SE) and *Staphyloccus aureus* (MRSA) when incubated in media comprised of 6 mM cysteine, 6 mM isoleucine, 6 mM leucine (i.e., 6 mM CIL) and 12 mM zinc carbonate, with or without 24 mM arginine bicarbonate at 37° C. for 72 hours, compared with negative control (water only)

| Bacteria | Time of Incubation | Plates | Media containing 6 mM Cys, 6 mM Leu, 6 mM Ileu, 12 mM zinc carbonate, 24 mM arginine bicarbonate | | | | | | | | | | | |
|---|---|---|---|---|---|---|---|---|---|---|---|---|---|---|
| | | | No additional medium added | | | | Additional same above media added in 24 and 48 hours | | | | Additional 24 mM arginine bicarbonate added in 24 and 48 hours | | | |
| | | | $10^4$ | $10^5$ | $10^6$ | $10^7$ | $10^4$ | $10^5$ | $10^6$ | $10^7$ | $10^4$ | $10^5$ | $10^6$ | $10^7$ |
| SE | 0 h | BHI | 9 | 8 | 8 | 8 | 9 | 8 | 8 | 8 | 9 | 8 | 8 | 8 |
| MRSA | | Blood | 10 | 9 | 8 | 8 | 10 | 9 | 8 | 8 | 10 | 9 | 8 | 8 |
| Mix | | Agar | 10 | 9 | 8 | 8 | 10 | 9 | 8 | 8 | 10 | 9 | 8 | 8 |
| | | CHRO | 10 | 9 | 8 | 8 | 10 | 9 | 8 | 8 | 10 | 9 | 8 | 8 |
| | | SE/SA % (~) | ... | ... | ... | ... | ... | ... | ... | ... | ... | ... | ... | ... |
| SE | 24 hr | BHI | 8 | 8 | 8 | 8 | 8 | 8 | 8 | 8 | 8 | 8 | 8 | 8 |
| MRSA | | Blood | 7 | 5 | 5 | 5 | 7 | 5 | 5 | 5 | 7 | 5 | 5 | 5 |
| Mix | | Agar | 8 | 7 | 5 | 5 | 8 | 7 | 5 | 5 | 8 | 7 | 5 | 5 |
| | | CHRO | 6 | 5 | 3 | 2 | 6 | 5 | 3 | 2 | 6 | 5 | 3 | 2 |
| | | SE/SA % (~) | 70/30 | 60/40 | 80/20 | 80/20 | ... | 60/40 | 80/20 | 80/20 | ... | 60/40 | 80/20 | 80/20 |
| SE | 48 h | BHI | 6 | 4 | 3 | 1 | 7 | 6 | 4 | 1 | 8 | 7 | 5 | 4 |
| MRSA | | Blood | 1 | 1 | 0 | 0 | 1 | 0 | 0 | 0 | 1 | 1 | 0 | 0 |
| Mix | | Agar | 1 | 0 | 0 | 0 | 5 | 1 | 1 | 0 | 7 | 5 | 1 | 1 |
| | | CHRO | 0 | 0 | 0 | 0 | 1 | 0 | 0 | 0 | 3 | 1 | 1 | 0 |
| | | SE/SA % (~) | ... | ... | ... | ... | 90/10 | ... | ... | ... | 90/10 | 90/10 | ... | ... |
| SE | 72 h | BHI | 5 | 5 | 4 | 3 | 6 | 5 | 4 | 2 | 7 | 5 | 4 | 4 |
| MRSA | | Blood | 0 | 0 | 0 | 0 | 0 | 0 | 0 | 0 | 0 | 0 | 0 | 0 |
| Mix | | Agar | 1 | 1 | 1 | 1 | 3 | 0 | 0 | 1 | 7 | 7 | 6 | 5 |
| | | CHRO | 0 | 1 | 1 | 0 | 0 | 0 | 0 | 0 | 5 | 5 | 4 | 1 |
| | | SE/SA % (~) | ... | ... | ... | ... | 100/0 | ... | ... | ... | 90/10 | 80/20 | 80/20 | 80/20 |

SE, *Staph. epidermidis*,
MRSA, *Staph. aureus* (MRSA),
Mix, mixture of *Staph. epidermidis* and *Staph. aureus* (MRSA),
CHRO, CHROMAgar medium plate selective for *Staph. aureus*, X, contamination
*Scale (0-10): 0, no colony; 1, <10; 2, 10-20; 3, 20-30; 4, 30-50; 5, 50-100; 6, 100-250; 7, 250-500; 8, >500; 9, colonies almost form a layer and are unable to count; 10, colonies form a layer Tables 1.4-1.6, above, include the following elements:
(a) Incubation of *Staph. epidermidis* and *Staph. aureus* and their combinations in the medium containing 12 mM zinc carbonate, 24 mM arginine bicarbonate, the CIL amino acids and their controls, showed:
  (i) *Staph. aureus* (MSSA or MRSA) quickly decreased, when incubated in the presence of arginine bicarbonate for 24 to 48 hours; all *Staph. aureus* organisms completely disappeared by 72 hours (see supporting FIGS. 1, 8, 16 and 19).
  (ii) *Staph. epidermidis* on the other hand decreased only slightly, when incubated with the medium containing arginine bicarbonate during the first 24 hours of incubation and decreased moderately or rapidly in the 48 to 72 hours thereafter (see relevant FIGS. 1, 2, 8, 9, 16 and 19).
  (iii) The mixture of *Staph. aureus* (MSSA or MRSA) and *Staph. epidermidis* also showed decreases, albeit only moderately, while being incubated in the medium containing arginine bicarbonate for 24 hours and where approximately 60-80% of survivors were *Staph. epidermidis*. The *Staph. aureus/Staph. epidermidis* mixture decreased quickly after 24 hours of incubation and almost all of the bacteria had disappeared by 72 hours (see FIGS. 3, 11, 18 and 22).
  (iv) In the negative control, both *Staph. aureus* (MSSA or MRSA) and *Staph. epidermidis* and the mixtures thereof incubated in sterile D-water, showed almost no reduction in 24 to 48 hours and very slight reduction in 48 to 72 hours (see FIGS. 1, 8, 16 and 19).
(b) Incubating *Staph. aureus* (MSSA or MRSA), *Staph. epidermidis* and their combinations in a medium containing the CIL amino acids, and zinc carbonate without arginine bicarbonate exhibited:
  (i) *Staph. aureus* (MSSA or MRSA) that showed no or slight reduction, while incubating for 24 to 48 hours and then decreased slightly or moderately thereafter. *Staph. aureus* showed much slower reduction of its numbers in the medium without arginine bicarbonate than when incubated in medium containing arginine bicarbonate (see FIGS. 2, 9, 17 and 20).
  (ii) *Staph. epidermidis* showed moderate to rapid reduction in numbers during incubation for 24 hours and disappeared after 48 hours (see FIGS. 2, 9, 17 and 20).
  (iii) Within 72 hours, the mixture of *Staph. aureus* (MSSA or MRSA) and *Staph. epidermidis* decreased moderately, while incubating in medium without arginine bicarbonate. Also, within 72 hours, approximately 70-90% of survivors were *Staph. aureus*, whereas in the mixture incubated in the medium containing arginine, bacteria correspondingly decreased slowly in 24 hours. About 70-75% of survivors were *Staph. epidermidis* and the mixture rapidly decreased in 48 to 72 hours. Almost all bacteria disappeared by 72 hours (see FIGS. 3, 11, 18, 22 and 23).
(c) The results of *Staph. aureus* (MRSA) and *Staph. epidermidis* being incubated in the medium including 12 mM zinc carbonate, 24 mM arginine bicarbonate, the CIL amino acids, and additional same medium or 24 mM arginine bicarbonate being added in 24 and 48 hours during 72 hours of incubation at 37° C. showed:
  (i) Slow *Staph. epidermidis* reduction during the first 24 hours and slower reduction after 48 to 72 hours, when additional same medium was added, at 24 and 48 hours. *Staph. epidermidis* even decreased, albeit more slowly, when additional 24 mM arginine bicarbonate was added after 24 and 48 hours, whereas *Staph. aureus* (MRSA) decreased, moderately to rapidly, after 48 hours with no microbial survivors after 72 hours. There were no differences among the incubation media and additional medium, whether arginine bicarbonate was or was not added (see FIG. 10 and Photo 21).
  (ii) The mixture of *Staph. aureus* (MRSA) and *Staph. epidermidis* decreased in a similar pattern, as did *Staph. epidermidis* with 60% of survivors being *Staph. epidermidis* after 24 hours of incubation and more than 90% *Staph. epidermidis* survivors after 48 to 72 hours of incubation (see FIG. 11 and Photo 23).
(d) *Staph. aureus* (MSSA or MRSA) was incubated with 12 mM zinc carbonate, 24 mM arginine bicarbonate and the CIL amino acids and decreased more and faster than being incubated in medium without arginine bicarbonate. This occurred within 72 hours of incubation, especially after 24 hours of incubation, when compared to samples diluted $10^4$ to $10^6$ (see FIGS. 4 and 12). In contrast, *Staph. epidermidis* decreased much less and more slowly in media containing arginine bicarbonate than being incubated in media without arginine bicarbonate, especially during 72 hours of incubation (see FIGS. 5 and 13).
(e) The pH values of *Staph. epidermidis*, *Staph. aureus* (MSSA or MRSA) and mixtures thereof, when incubated with zinc carbonate, CIL and with or without arginine bicarbonate, and additional same medium or 24 mM arginine bicarbonate being added at 24 and 48 hours during 72 hours of incubation at 37° C., in comparison to a negative control (see FIGS. 7 and 15).
  (i) pH values of SE, SA and their mixture incubated in media containing arginine bicarbonate were stable at pH 8.3 to 8.6.
  (ii) pH values of SE, SA and their mixture incubated in media without arginine bicarbonate stayed at lower pH levels i.e. 6.1 to 6.8.
  (iii) Bacteria incubated in sterile distilled water that served as negative controls, had similar pH values, as counterpart bacteria incubated in media without arginine bicarbonate at pH 6.0 to 6.4.

Discussion

Figure 2:
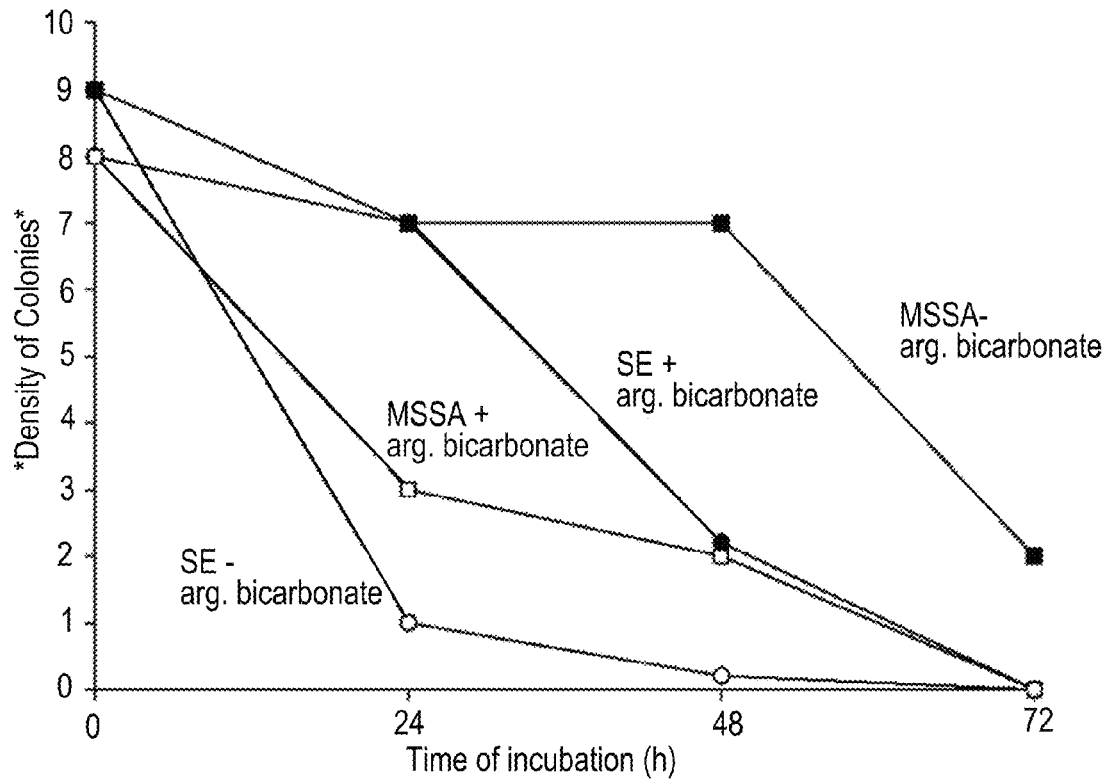
FIG. 2 is a graph showing the effect of arginine bicarbonate on the growth of 8.3% (v/v) *Staphylococcus aureus* (MSSA), compared to 8.3% (v/v) *Staphylococcus epidermidis*, incubated with 12.0 mM zinc carbonate and 6.0 mM CIL, with or without 24.0 mM arginine bicarbonate at 37° C. for 72 hours.
Figure 3:
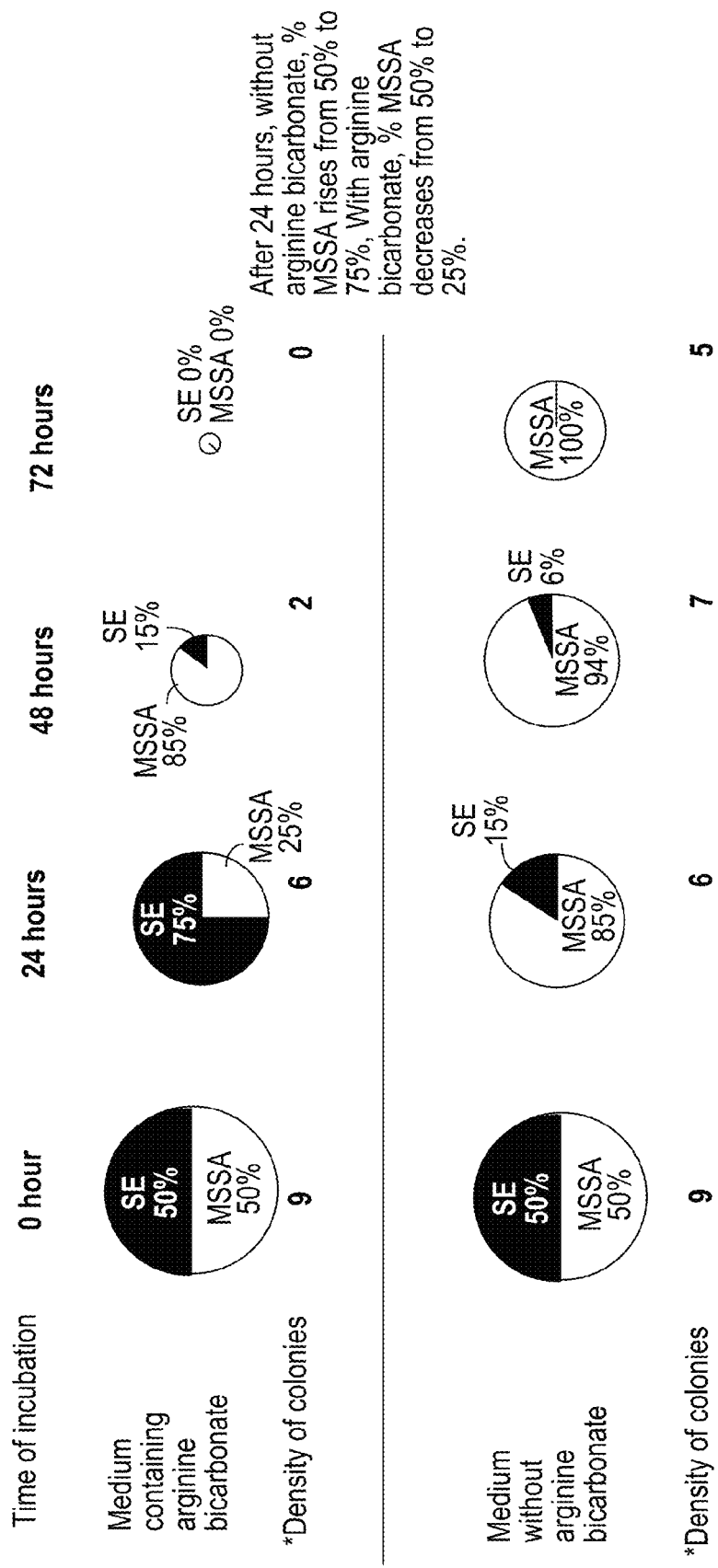
FIG. 3 is a graph showing the effect of arginine bicarbonate on the growth of an 8.3% (v/v) 1:1 mixture of *Staphylococcus epidermidis* and *Staphylococcus aureus* (MSSA) incubated with 12.0 mM zinc carbonate and 6.0 mM CIL, with or without 24.0 mM arginine bicarbonate, at 37° C. for 72 hours.
Figure 4:
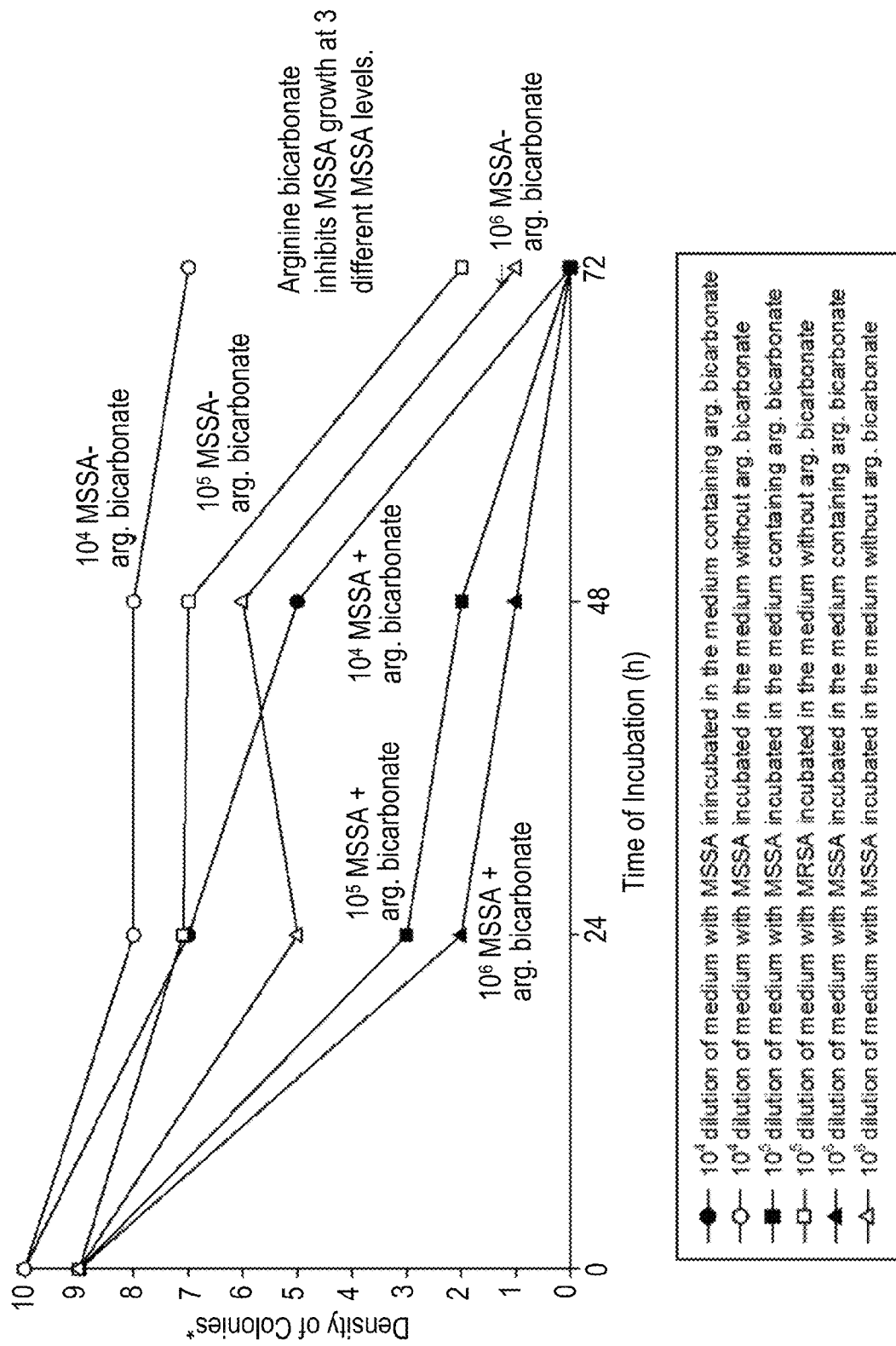
FIG. 4 is a graph showing the effect of arginine bicarbonate on the growth of 8.3% (v/v) *Staphylococcus aureus* (MSSA) incubated with 12.0 mM zinc carbonate and 6.0 mM CIL, with or without 24.0 mM arginine bicarbonate, at 37° C. for 72 hours.
Figure 8:
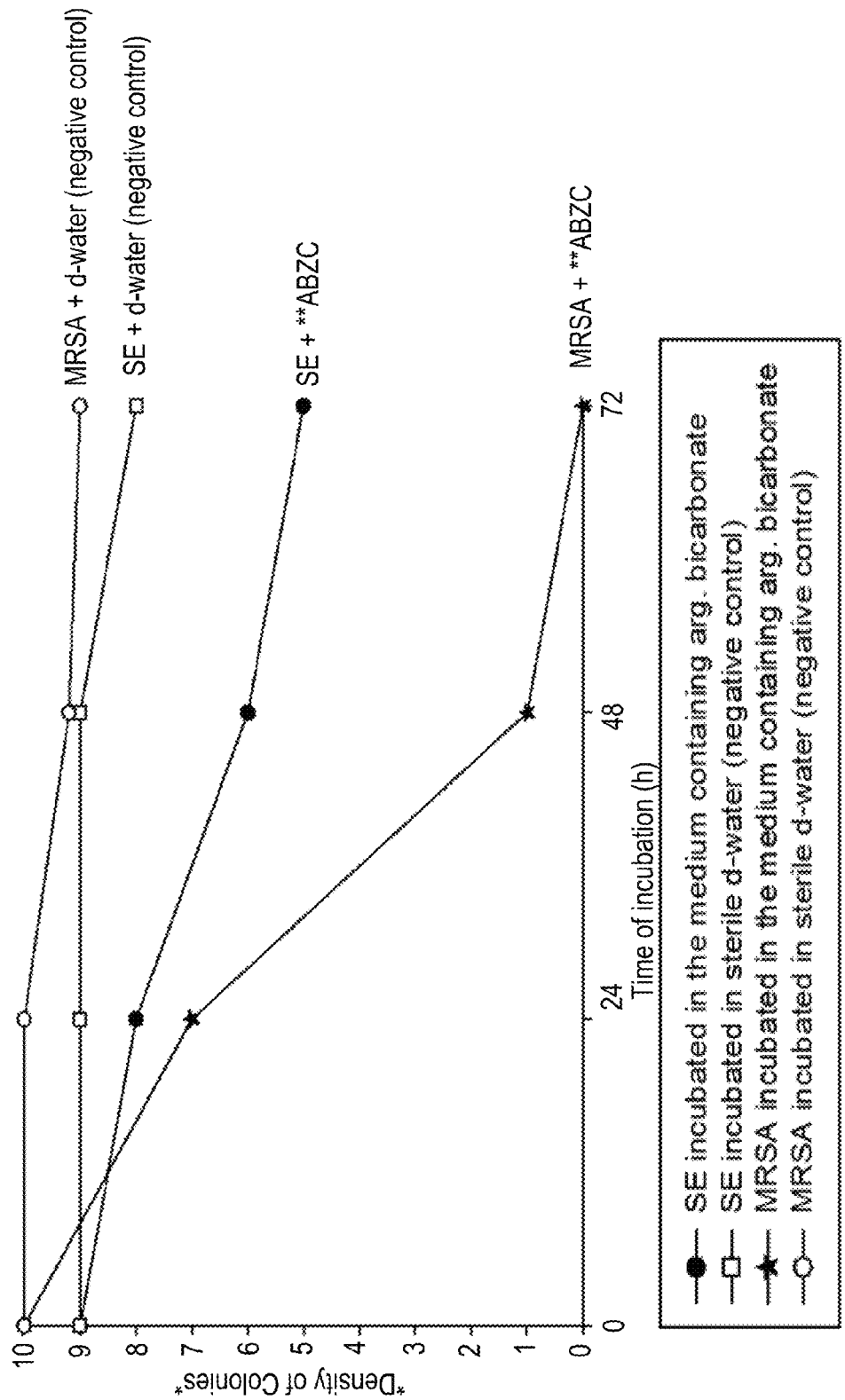
FIG. 8 is a graph showing the effect of arginine bicarbonate on the growth of 8.3% (v/v) *Staphylococcus epidermidis* or 8.3% (v/v) *Staphylococcus aureus* (MRSA) incubated with 12.0 mM zinc carbonate, 6.0 mM CIL and 24.0 mM arginine bicarbonate at 37° C. for 72 hours.
Figure 9:
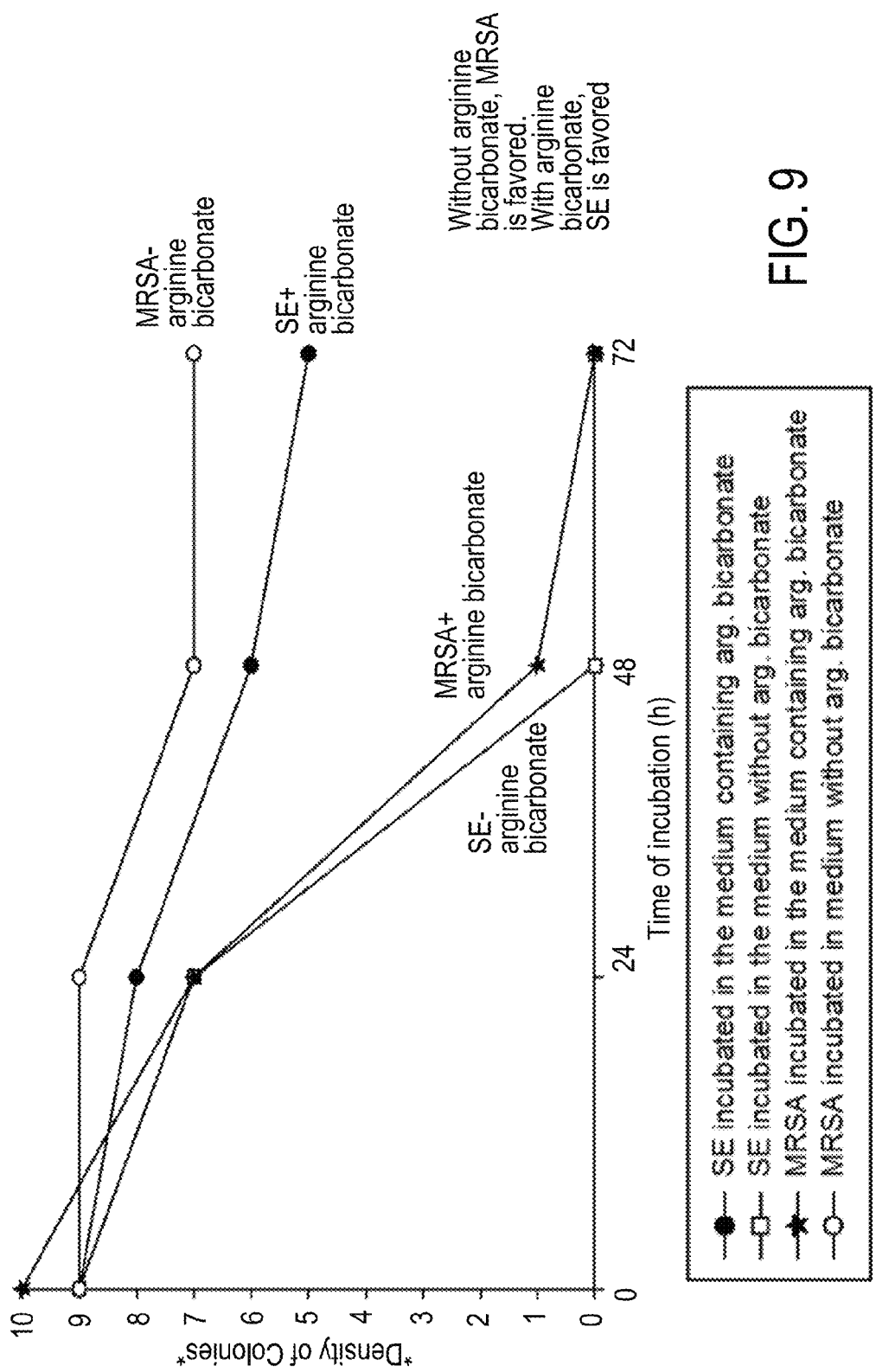
FIG. 9 is a graph showing the effect of arginine bicarbonate on the growth of 8.3% (v/v) *Staphylococcus aureus* (MRSA), compared to 8.3% (v/v) *Staphylococcus epidermidis*, incubated with 12.0 mM zinc carbonate and 6.0 mM CIL, with or without 24.0 mM arginine bicarbonate, at 37° C. for 72 hours.
Figure 10:
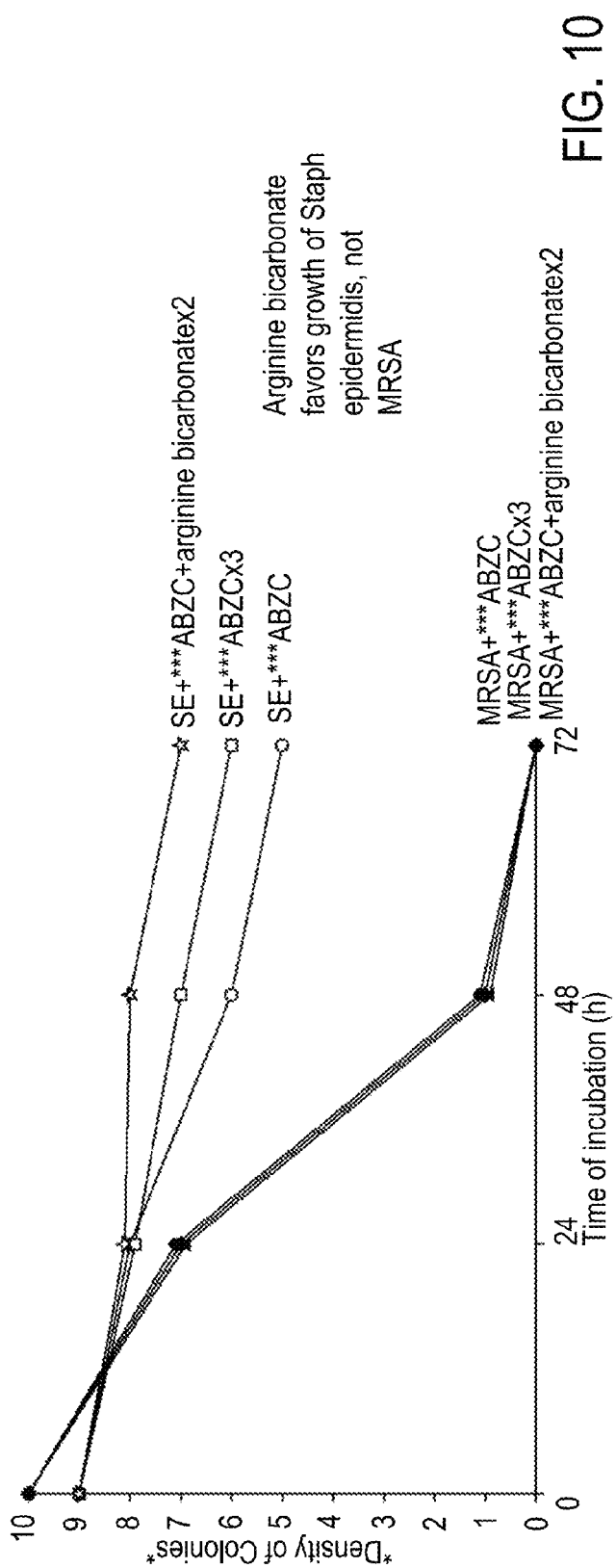
FIG. 10 is a graph showing the effect of arginine bicarbonate on the growth of 8.3% (v/v) *Staphylococcus epidermidis* or 8.3% (v/v) *Staphylococcus aureus* (MRSA) incubated with 12.0 mM zinc carbonate, 6.0 mM CIL and 24.0 mM arginine bicarbonate, and modified versions of this medium, at 37° C. for 72 hours.
Figure 11:
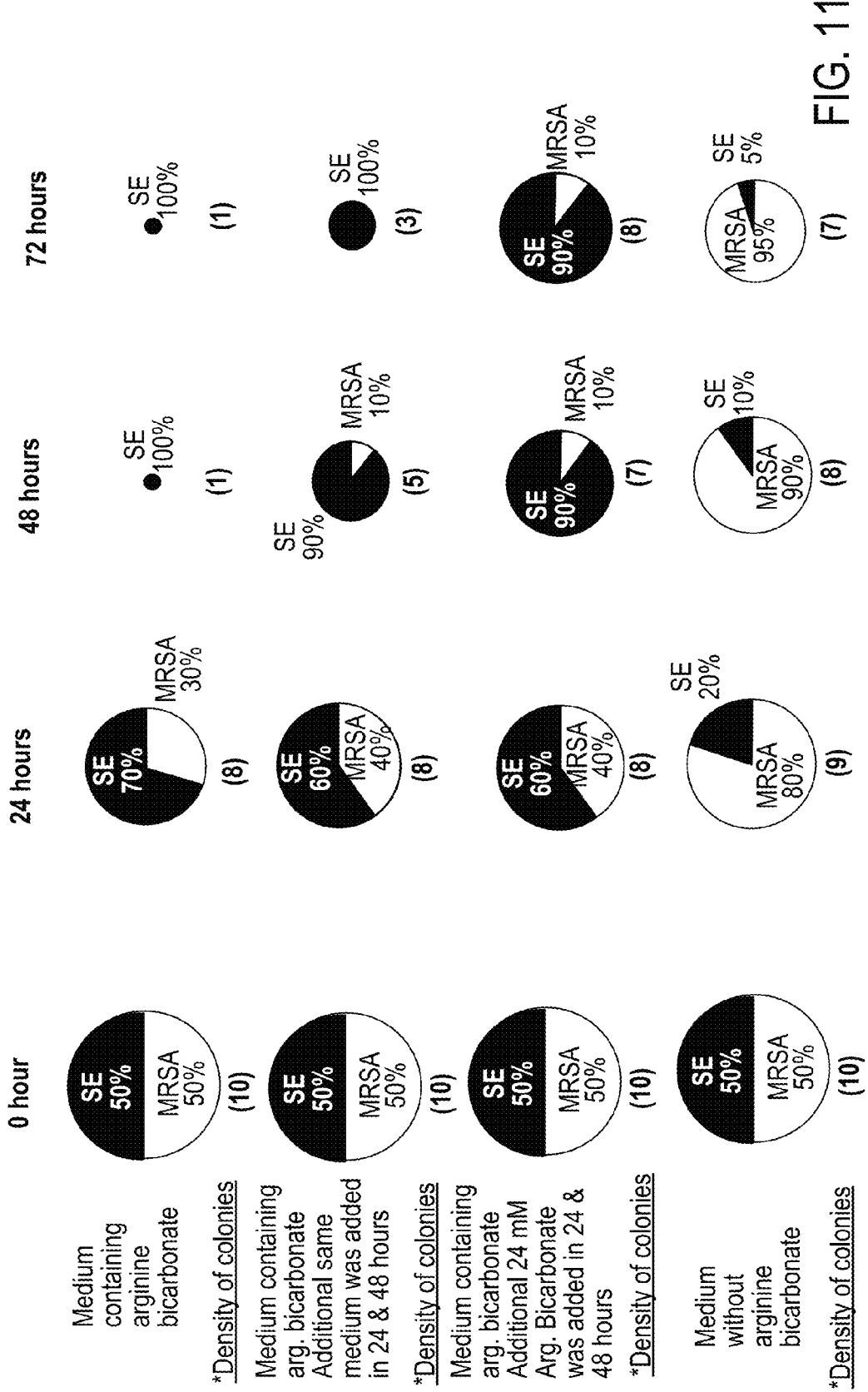
FIG. 11 is a graph showing the effect of arginine bicarbonate on the growth of an 8.3% (v/v) 1:1 mixture of *Staphylococcus aureus* (MRSA) and *Staphylococcus epidermidis* incubated with 12.0 mM zinc carbonate and 6.0 mM CIL, with or without 24.0 mM arginine bicarbonate, and modified versions of this medium, 37° C. for 72 hours.
Figure 12:
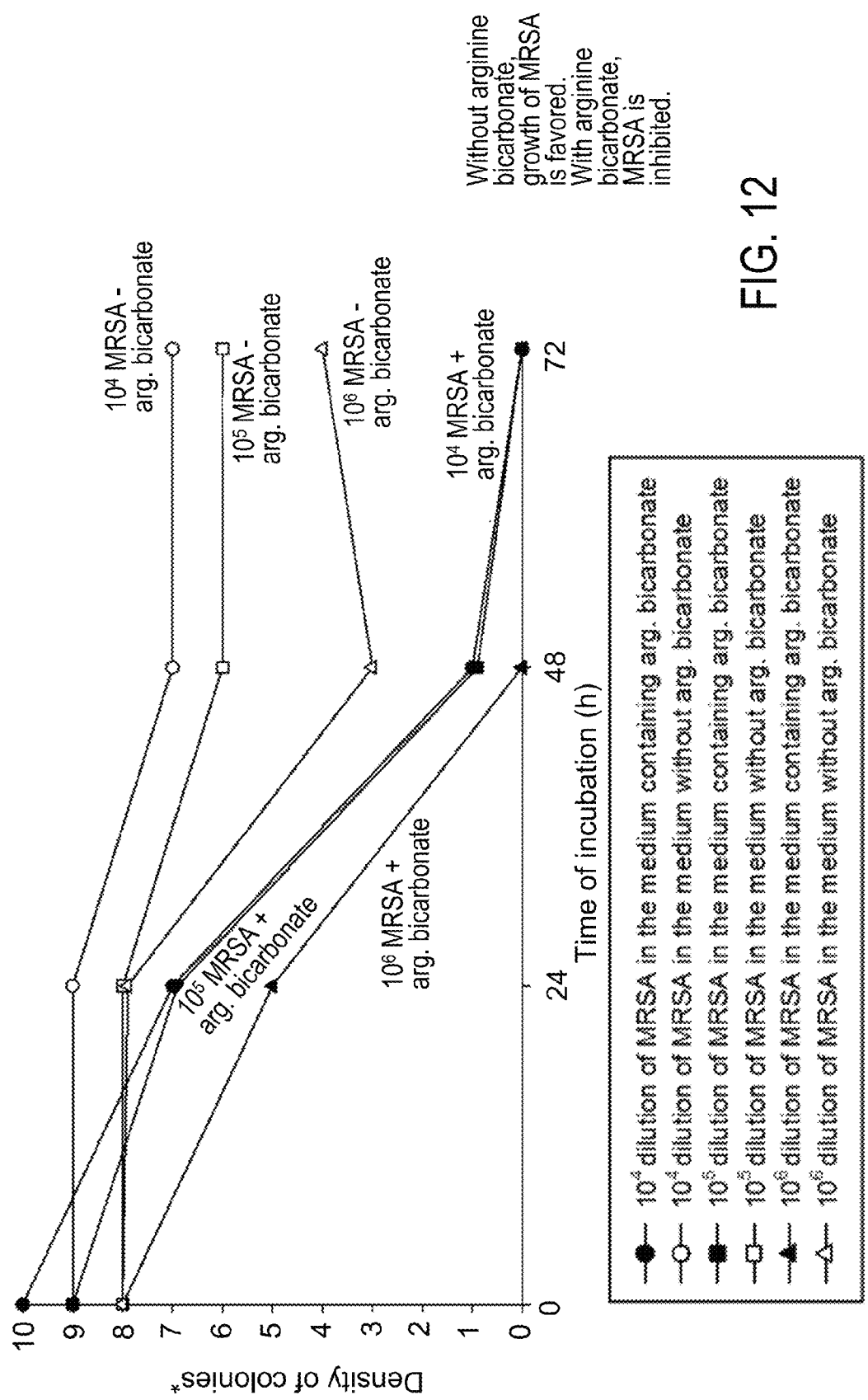
FIG. 12 is a graph showing the effect of arginine bicarbonate on the growth of 8.3% (v/v) *Staphylococcus aureus* (MRSA) incubated at various dilutions with 12.0 mM zinc carbonate and 6.0 mM CIL, with or without 24.0 mM arginine bicarbonate, at 37° C. for 72 hours.

The results obtained in the experiments above demonstrated that a medium of 12 mM zinc carbonate, 24 mM arginine bicarbonate and 6 mM CIL (i.e., 6 mM of each of cysteine, isoleucine and leucine), when incubated in a water bath at 37° C. for 72 hours, was able to bring about a decrease in both *Staph. epidermidis* (SE) and *Staph. aureus* (MSSA or MRSA) levels (FIGS. 1 and 8). However, such a medium favored much of a reduction of *Staph. aureus* (MSSA or MRSA) and did so significantly more rapidly than reduction of *Staph. epidermidis* (FIGS. 2 and 9). The number of both bacteria decreased sharply after 24 hours of incubation (FIGS. 2 and 9). This appeared to be due to substrate depletion, since addition of arginine bicarbonate to the medium during the *Staph. epidermidis* incubation only decreased its numbers slightly (FIG. 10). To be noted, *Staph. aureus* (MRSA) showed no positive selection at all. Almost all of the *Staph. aureus* (MRSA) bacteria involved had disappeared after 48 to 72 hours (FIG. 10).

In contrast (see FIGS. 4, 5, 12 and 13), when *Staph. epidermidis* was incubated without arginine bicarbonate present, its numbers decreased much sooner than when the medium contained arginine bicarbonate. *Staph. aureus* (MSSA or MRSA) showed opposite results.

This implies that the medium containing 12.0 mM zinc carbonate, 24.0 mM arginine bicarbonate and 6.0 mM CIL amino acids was able to inhibit the growth of *Staph. aureus* (MSSA or MRSA), while maintaining growth of *Staph. epidermidis*. In other words and needing emphasis is that arginine bicarbonate was able to support the growth of *Staph. epidermidis*, while not similarly benefiting *Staph. aureus* (MSSA or MRSA) at all.

Figure 5:
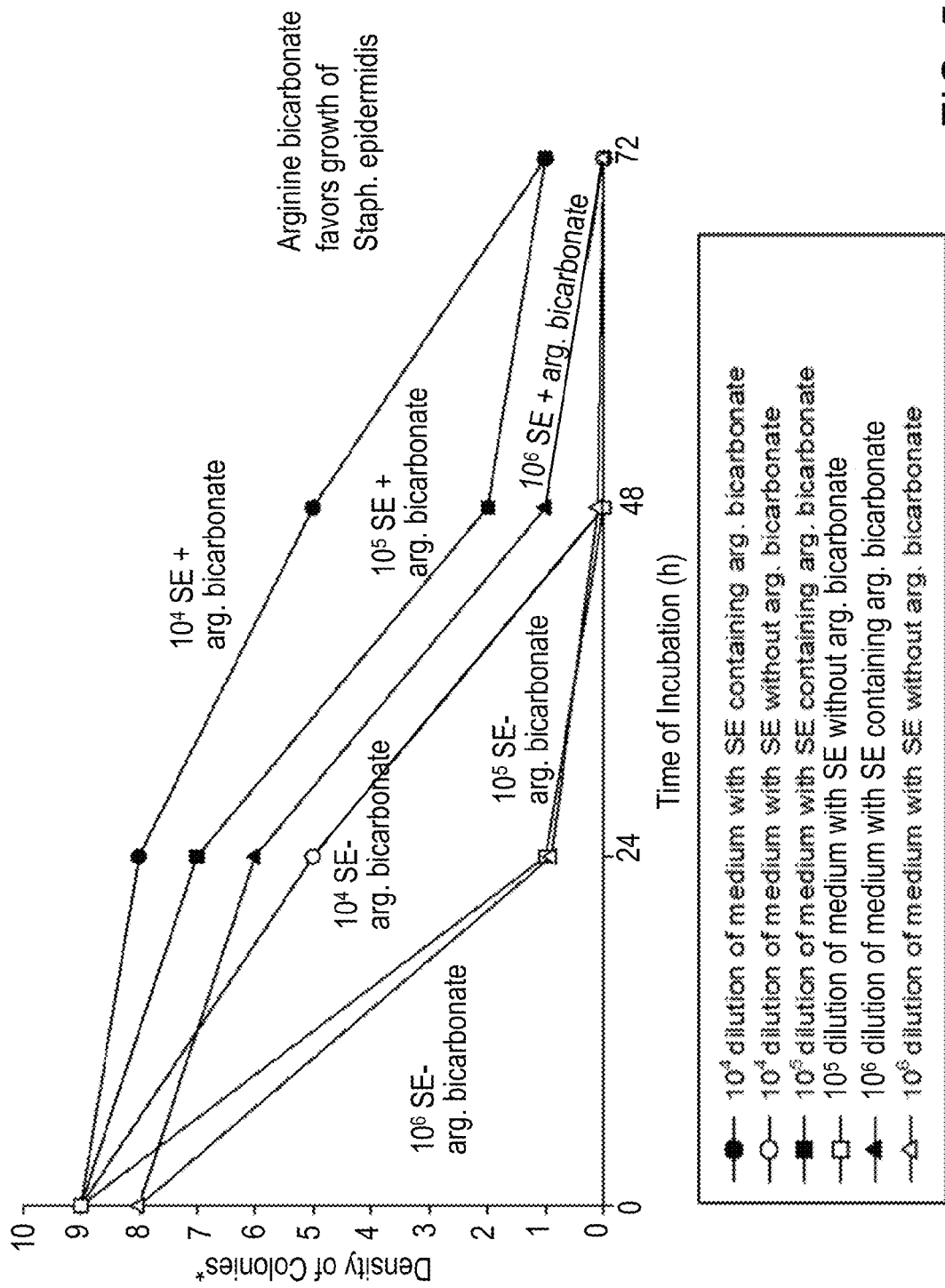
FIG. 5 is a graph showing the effect of arginine bicarbonate on the growth of 8.3% (v/v) *Staphylococcus epidermidis* incubated with 12.0 mM zinc carbonate and 6.0 mM CIL, with or without 24.0 mM arginine bicarbonate, at 37° C. for 72 hours.
Figure 6:
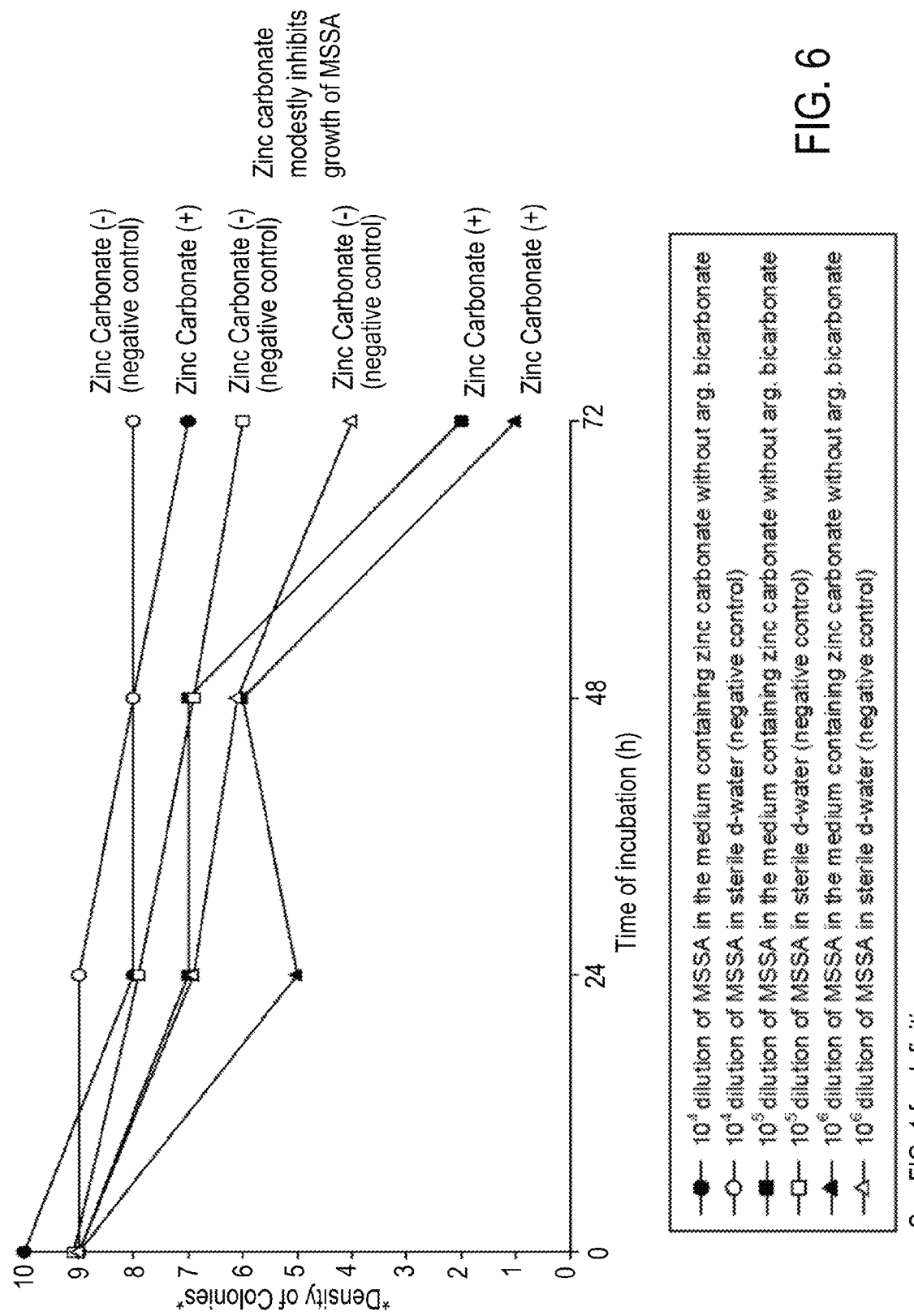
FIG. 6 is a graph showing the effect of zinc carbonate on the growth of 8.3% (v/v) *Staphylococcus aureus* (MSSA) incubated with 12.0 mM zinc carbonate and 6.0 mM CIL at 37° C. for 72 hours.
Figure 7:
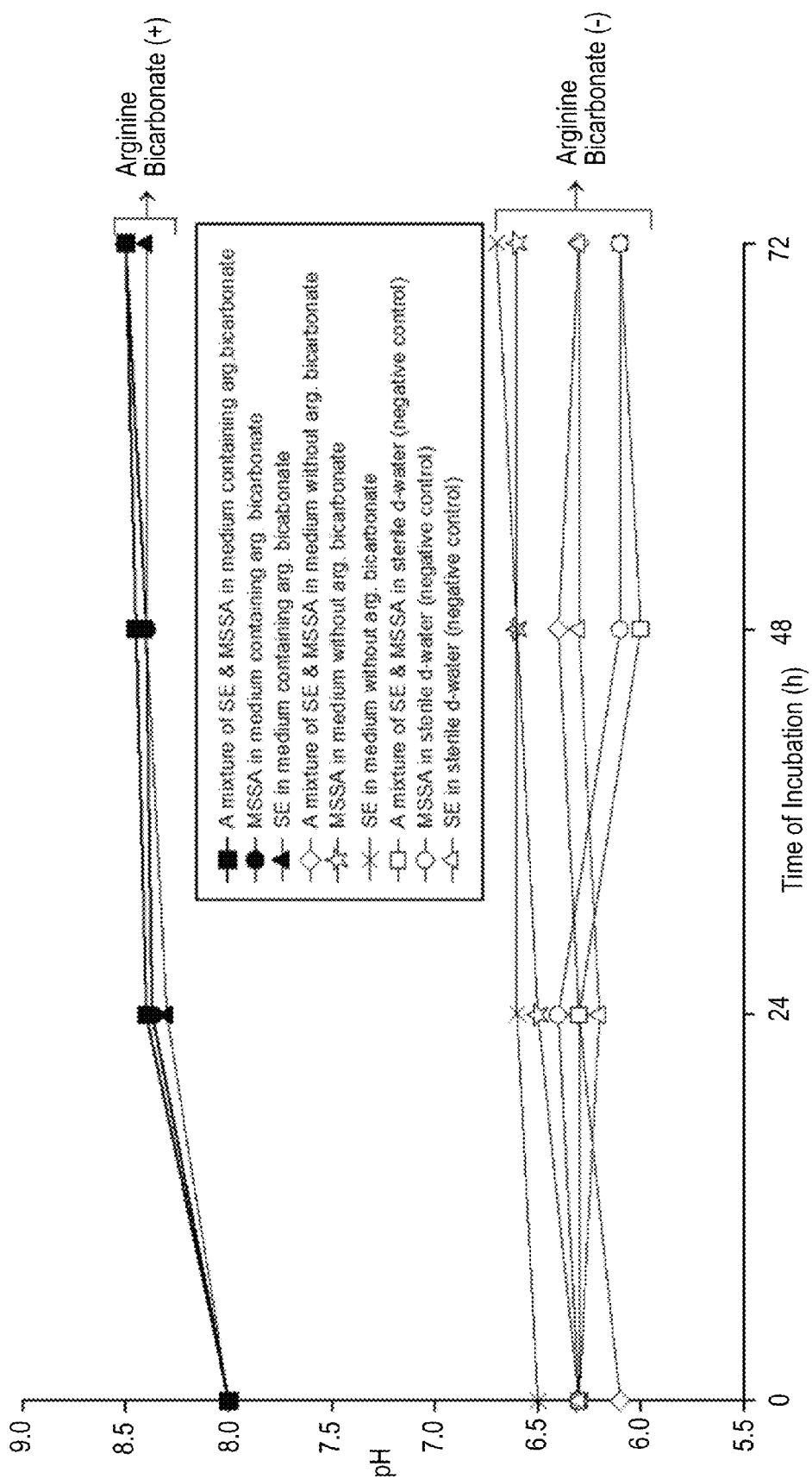
FIG. 7 is a graph showing the effect of arginine bicarbonate on the pH and growth of 8.3% (v/v) *Staphylococcus aureus* (MSSA), 8.3% (v/v) *Staphylococcus epidermidis* or an 8.3% (v/v) 1:1 mixture of *Staphylococcus aureus* (MSSA) and *Staphylococcus epidermidis* incubated with 12.0 mM zinc carbonate and 6.0 mM CIL, with or without 24.0 mM arginine bicarbonate, at 37° C. for 72 hours.
Figure 13:
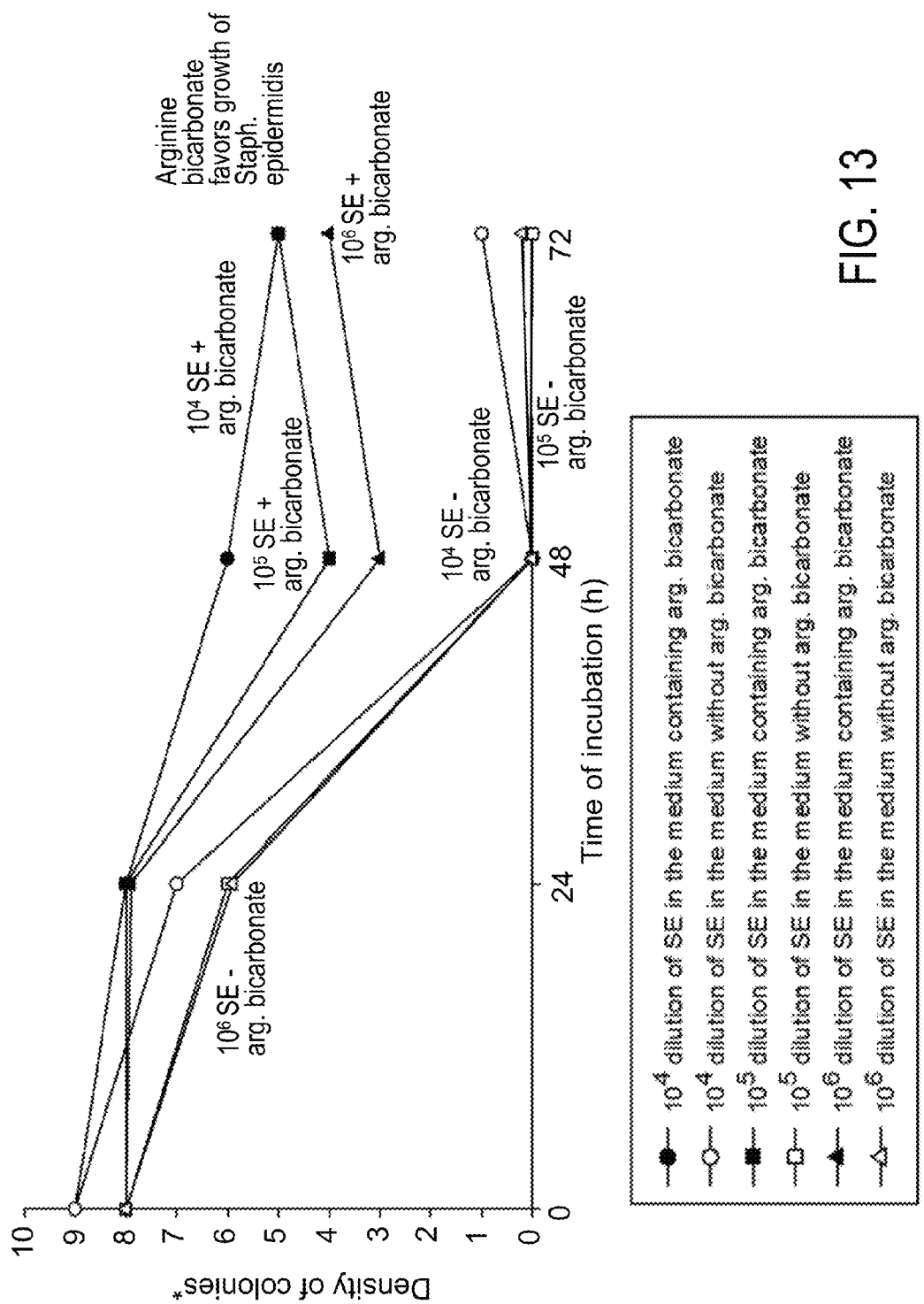
FIG. 13 is a graph showing the effect of arginine bicarbonate on live growth of 8.3% (v/v) *Staphylococcus epidermidis* incubated at various dilutions with 12.0 mM zinc carbonate and 6.0 mM CIL, with or without 24.0 mM arginine bicarbonate, at 37° C. for 72 hours.
Figure 14:
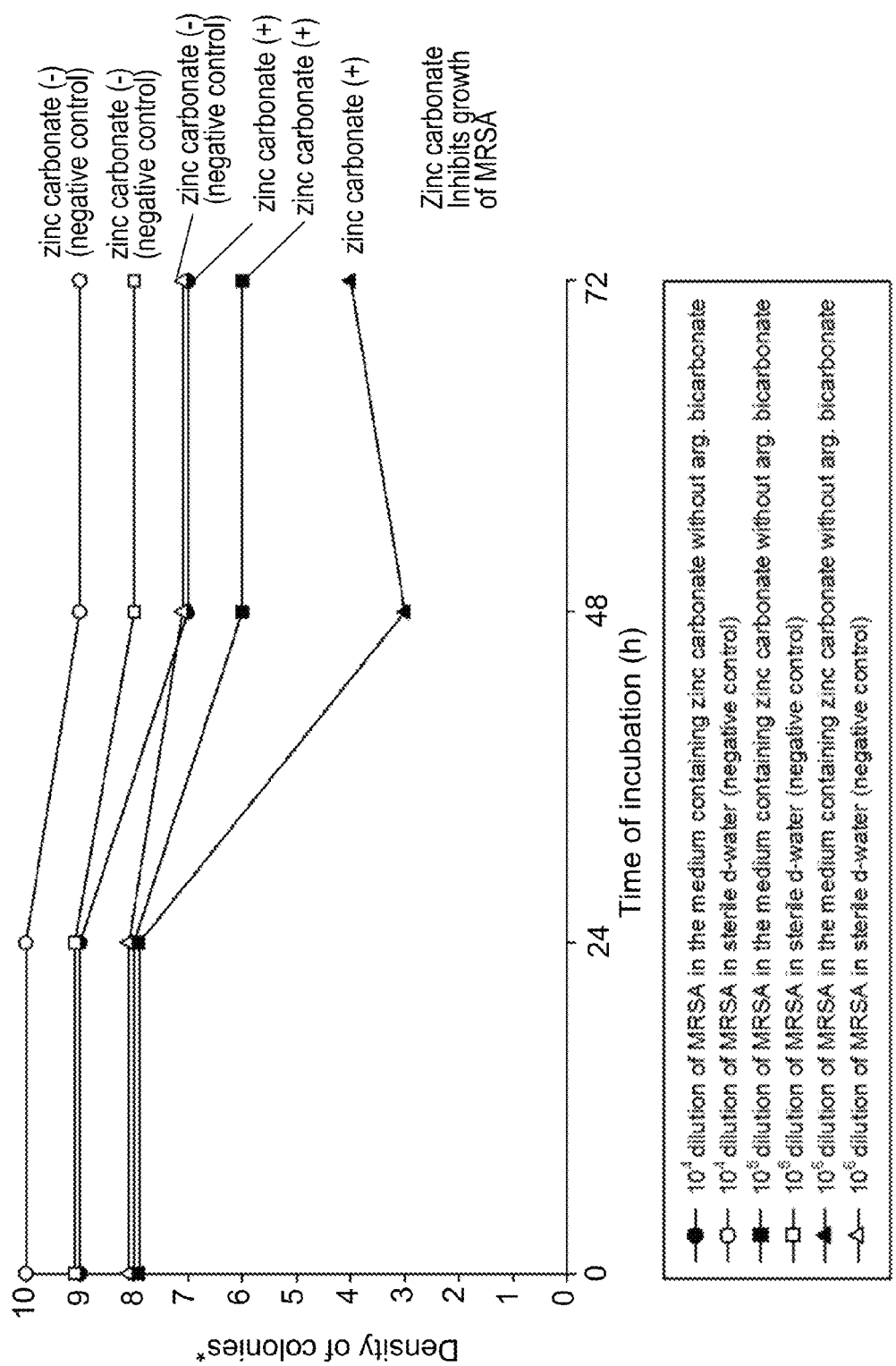
FIG. 14 is a graph showing the effect of zinc carbonate on the growth of 8.3% (v/v) Staphylococcus aureus (MRSA) incubated at various dilutions with 12.0 mM zinc carbonate and 6.0 mM CIL at 37° C. for 72 hours.
Figure 15:
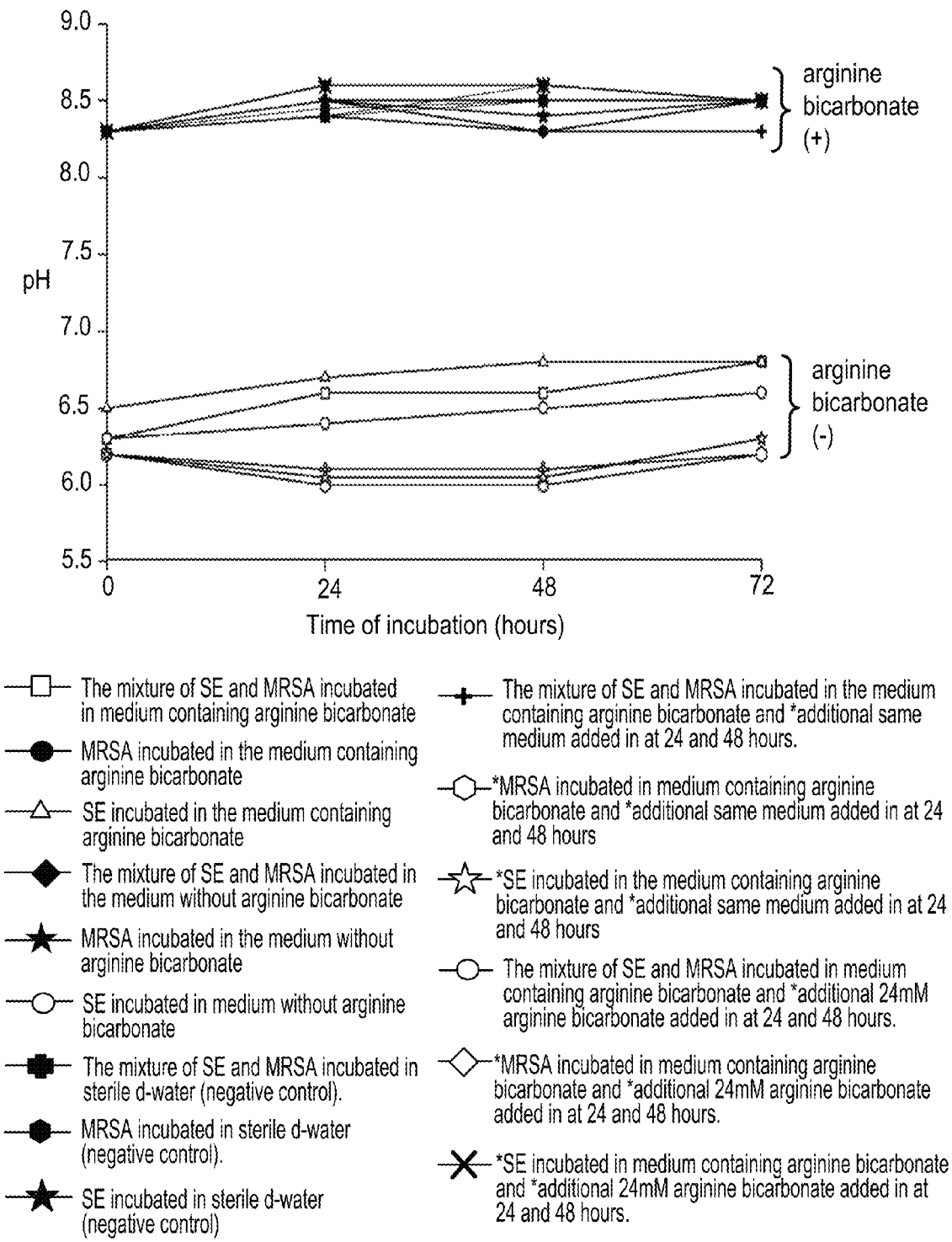
FIG. 15 is a graph showing the pH responses of 8.3% (v/v) Staphlococcus epidermidis, 8.3% Staphylococcus aureus (MRSA) or an 8.3% (v/v) 1:1 mixture of Staphylococcus epidermidis and Staphylococcus aureus (MRSA) to 12.0 mM zinc carbonate and 6.0 mM CIL, with or without 24.0 mM arginine bicarbonate, and modified versions of this medium, at 37° C. for 72 hours.
Figure 16:
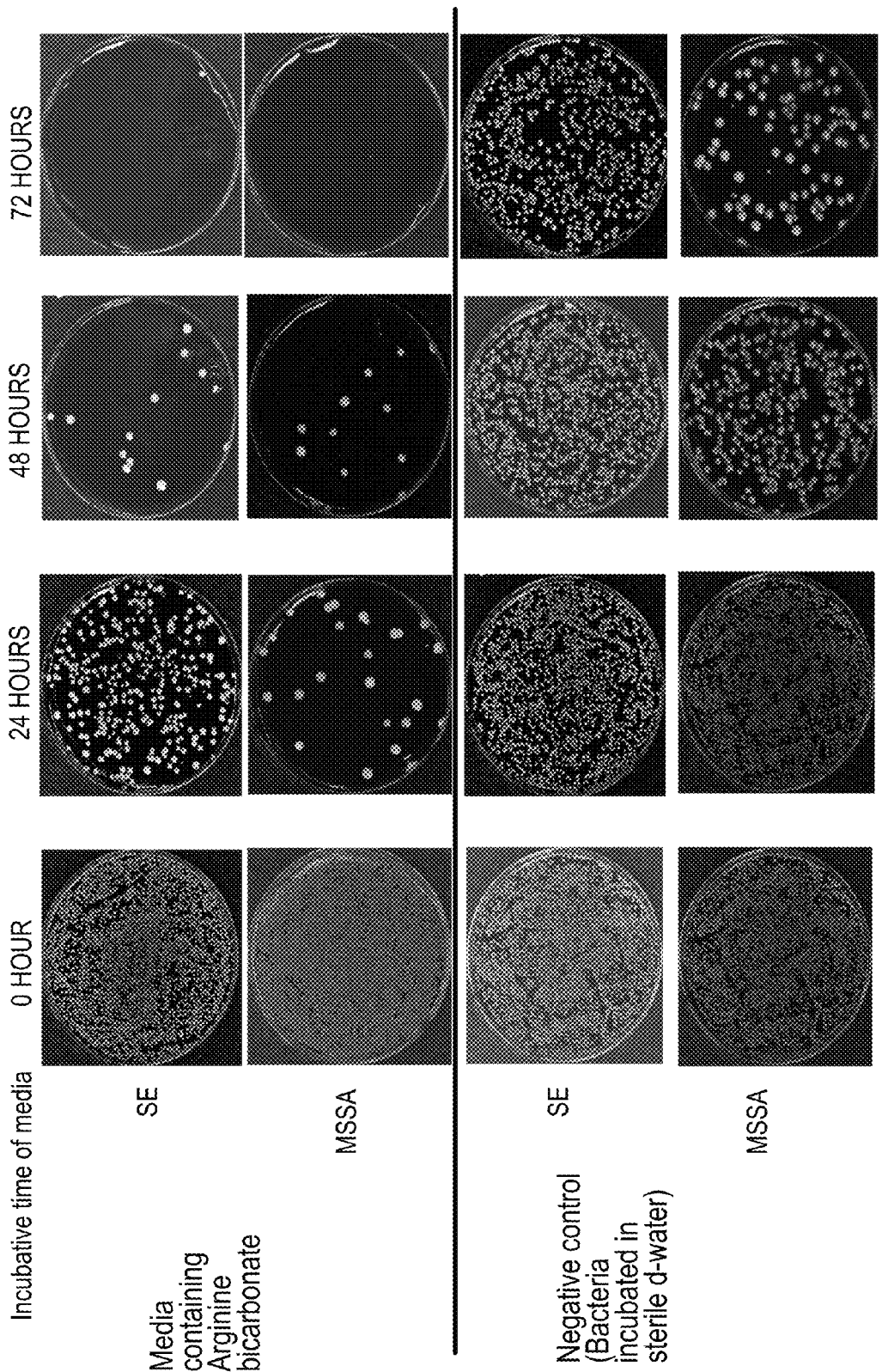
FIG. 16 is a photograph showing the effect of 24.0 mM arginine bicarbonate on the growth of 8.3% (v/v) Staphylococcus epidermidis or 8.3% (v/v) Staphylococcus aureus (MSSA) incubated with 12.0 mM zinc carbonate, 6.0 mM CIL and 24.0 mM arginine bicarbonate, at 37° C. for 72 hours.
Figure 17:
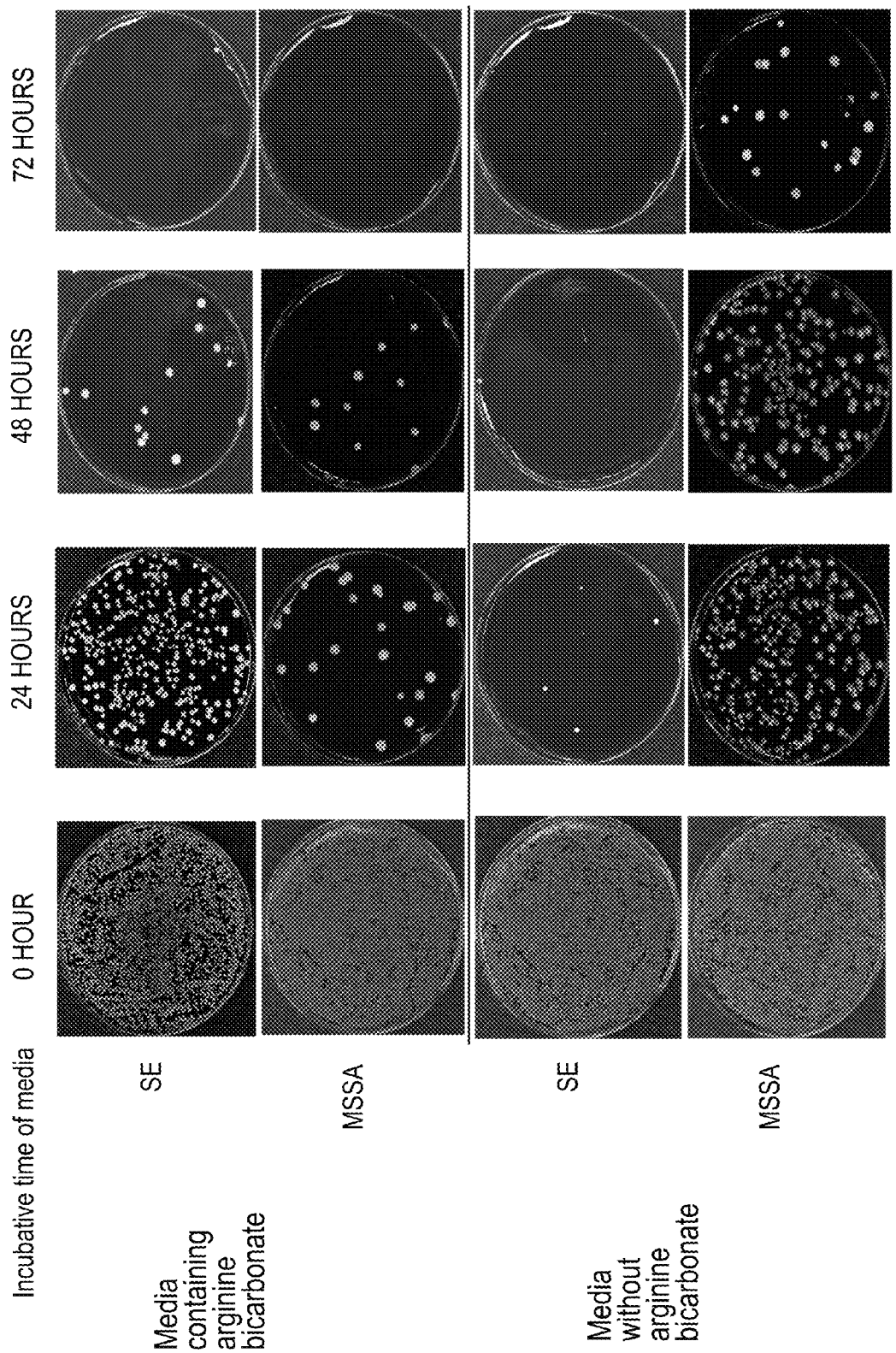
FIG. 17 is a photograph showing the effect of 24.0 mM arginine bicarbonate on the growth of 8.3% (v/v) Staphylococcus epidermidis or 8.3% (v/v) Staphylococcus aureus (MSSA) incubated with 12.0 mM zinc carbonate and 6.0 mM CIL, with or without 24.0 mM arginine bicarbonate, at 37° C. for 72 hours.
Figure 18:
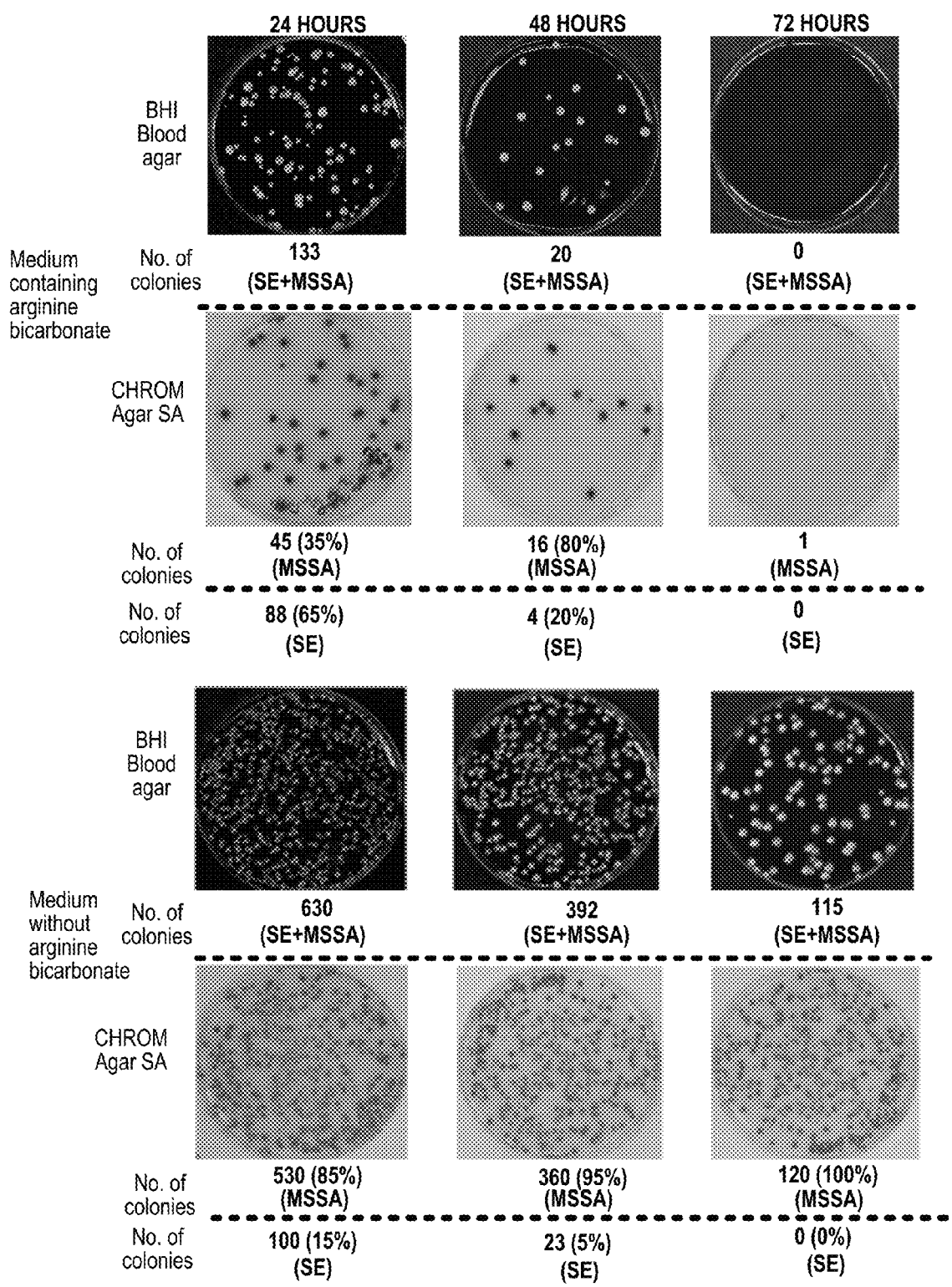
FIG. 18 is a photograph showing the effect of 24.0 mM arginine bicarbonate on the growth of an 8.3% (v/v) 1:1 mixture of Staphylococcus epidermidis and Staphylococcus aureus (MSSA) incubated with 12.0 mM zinc carbonate and 6.0 mM CIL, with or without 24.0 mM arginine bicarbonate, at 37° C. for 72 hours.
Figure 19:
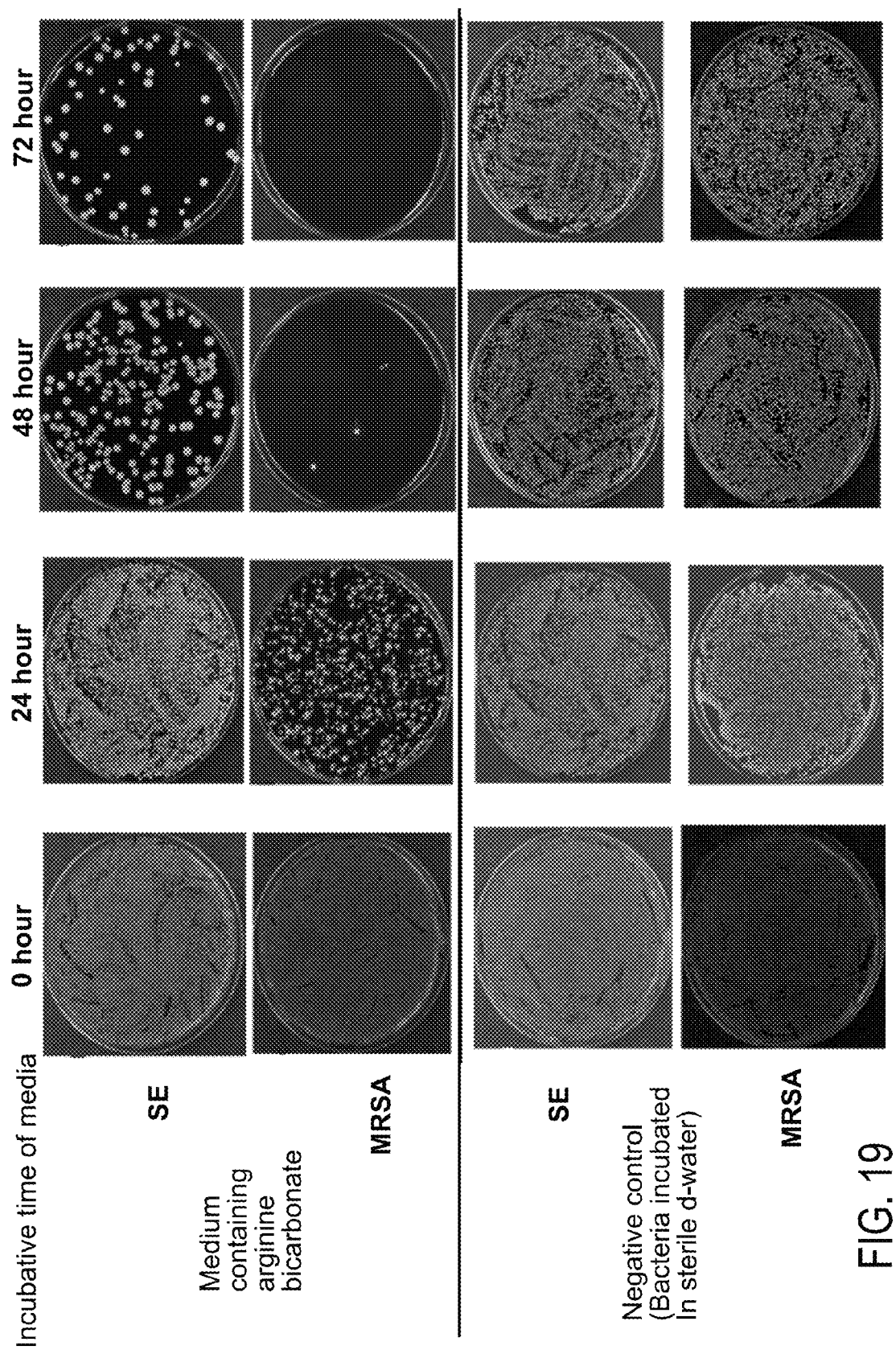
FIG. 19 is a photograph showing the effect of 24.0 mM arginine bicarbonate on the growth of 8.3% (v/v) Staphylococcus epidermidis or 8.3% (v/v) Staphylococcus aureus (MRSA) incubated with 12.0 mM zinc carbonate, 6.0 mM CIL and 24.0 mM arginine bicarbonate, at 37° C. for 72 hours.
Figure 20:
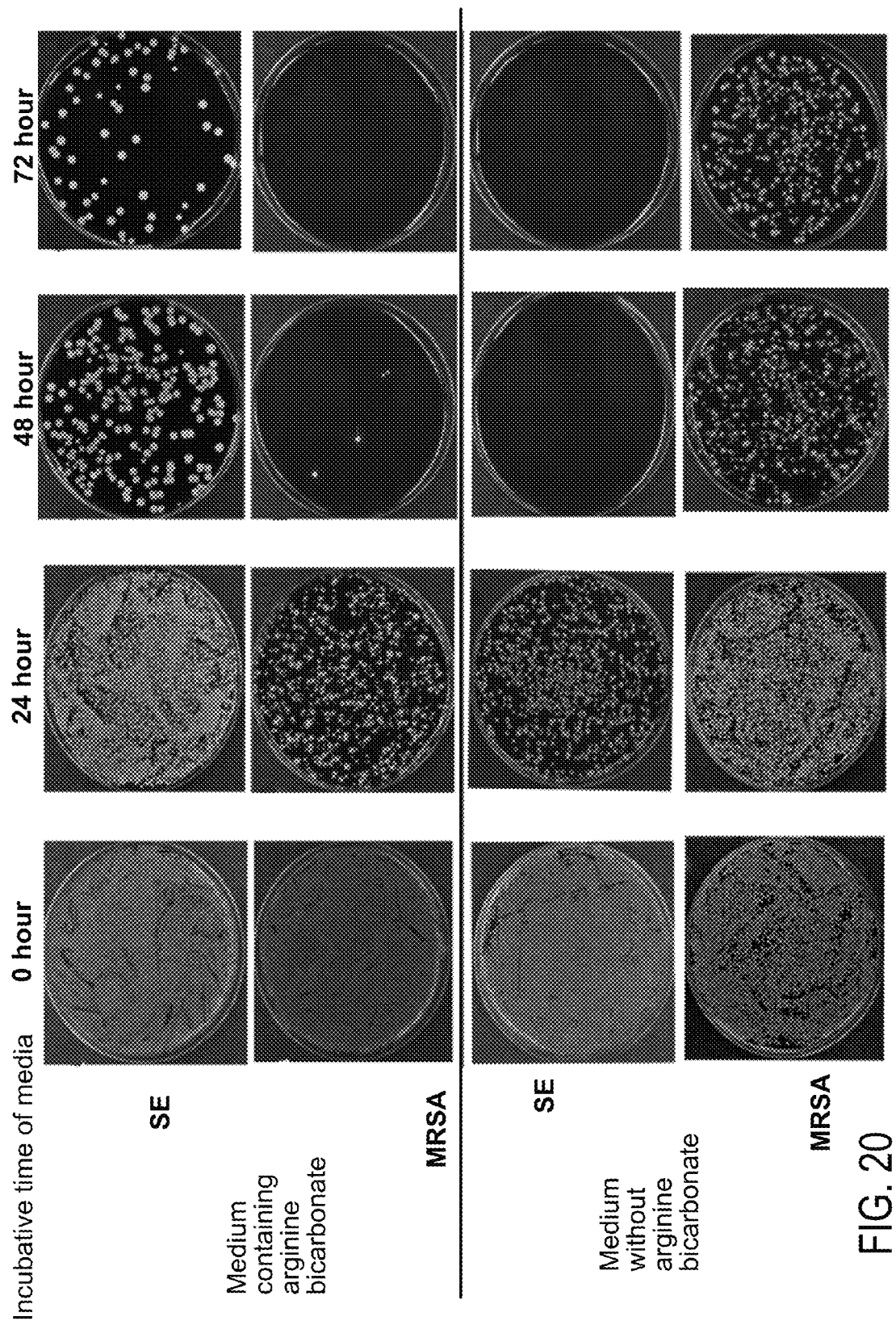
FIG. 20 is a photograph showing the effect of 24.0 mM arginine bicarbonate on the growth of 8.3% (v/v) Staphylococcus epidermidis or 8.3% (v/v) Staphylococcus aureus (MRSA) incubated with 12.0 mM zinc carbonate and 6.0 mM CIL, with or without 24.0 mM arginine bicarbonate, at 37° C. for 72 hour.
Figure 21:
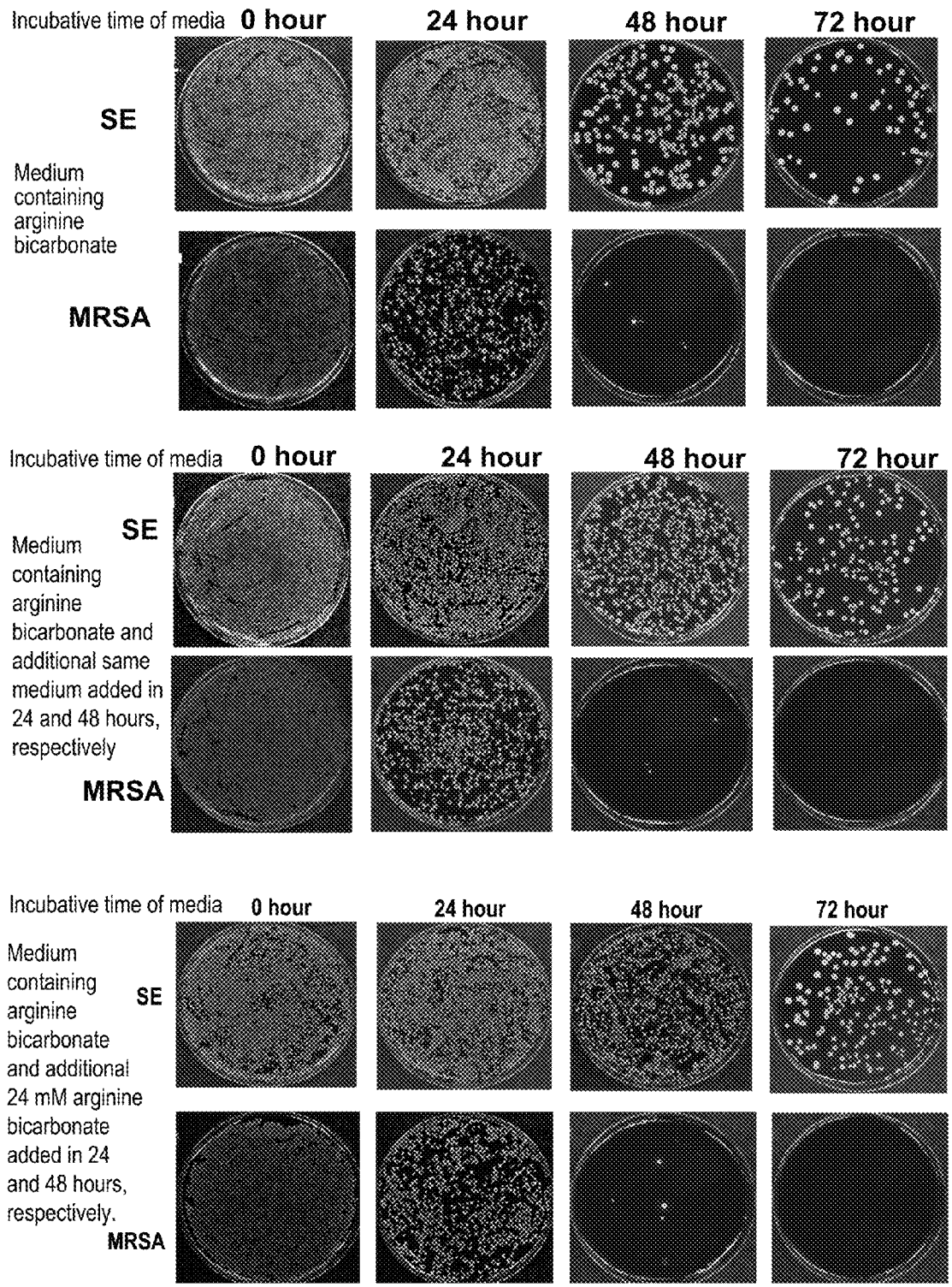
FIG. 21 is a photograph showing the effect of 24.0 mM arginine bicarbonate on the growth of 8.3% (v/v) Staphylococcus epidermidis or 8.3% (v/v) Staphylococcus aureus (MRSA) incubated with 12.0 mM zinc carbonate, 6.0 mM CIL and 24.0 mM arginine bicarbonate, and modified versions of this medium, at 37° C. for 72 hours.
Figure 22:
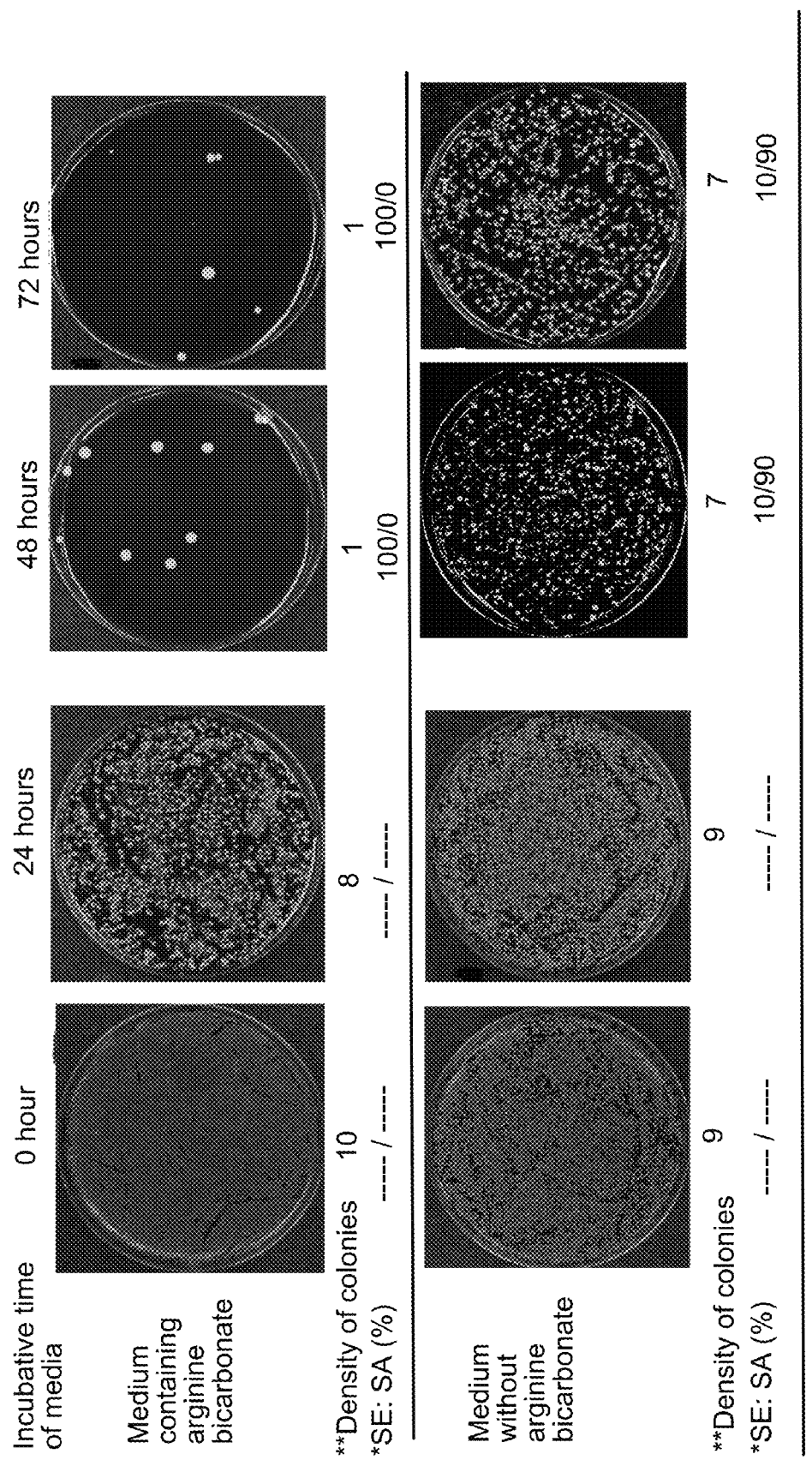
FIG. 22 is a photograph showing the effect of 24.0 mM arginine bicarbonate on the growth of an 8.3% (v/v) 1:1 mixture of Staphylococcus epidermidis and Staphylococcus aureus (MRSA) incubated with 12.0 mM zinc carbonate and 6.0 mM CIL, with or without 24.0 mM arginine bicarbonate, at 37° C. for 72 hours.
Figure 23:
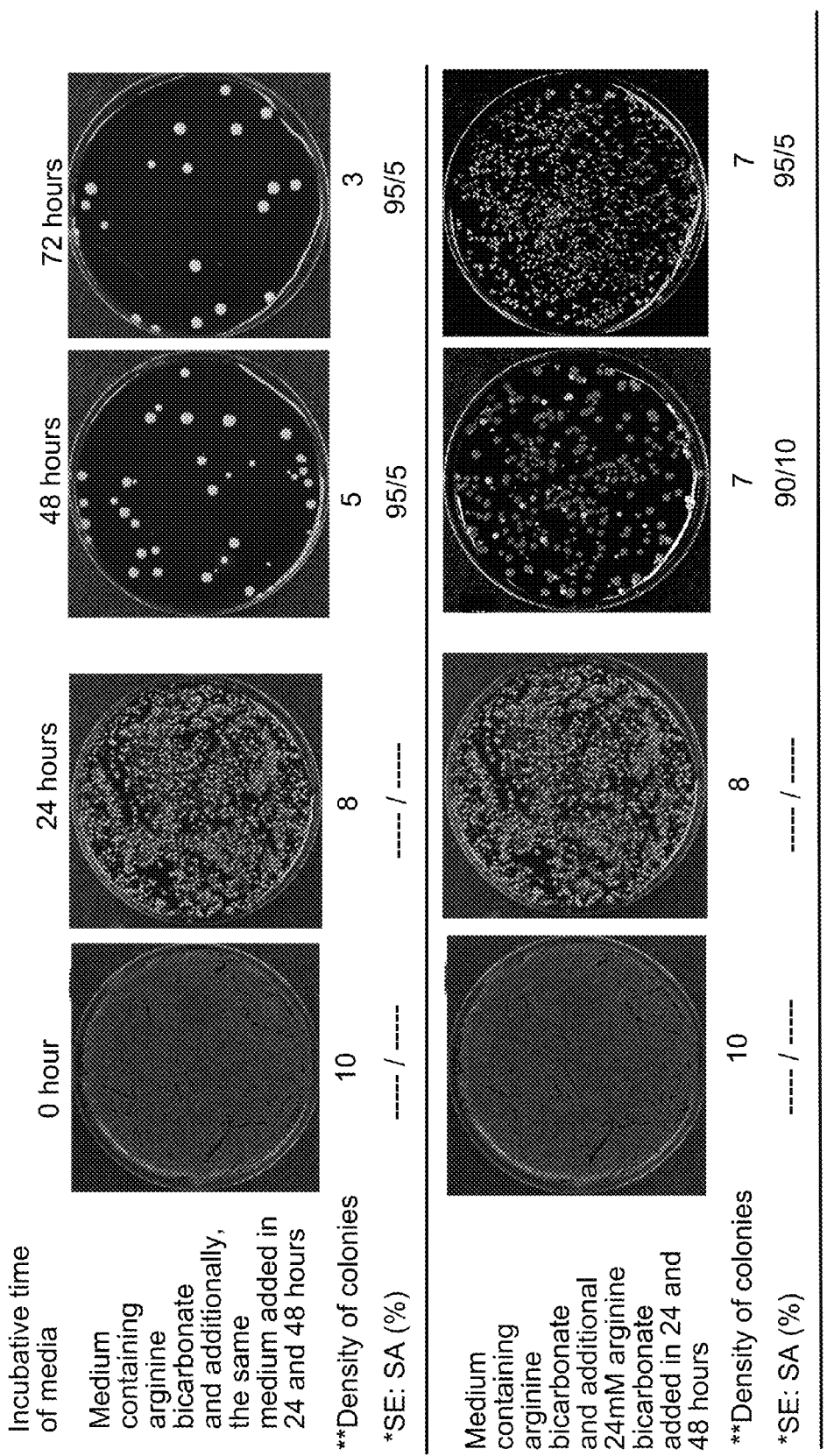
FIG. 23 is a photograph showing the comparison of the effect of arginine bicarbonate on the growth of an 8.3% (v/v) 1:1 mixture of Staphylococcus epidermidis and Staphylococcus aureus (MRSA). The medium used at the start of each experiment was 12.0 mM zinc carbonate, 6.0 mM CIL and 24.0 mM arginine bicarbonate, incubated at 37° C. for 72 hours. The top series of photographs show that at 24 and 48 hours, additional medium (12.0 mM zinc carbonate, 6.0 mM CIL and 24.0 mM arginine bicarbonate) was added. The bottom series of photographs show that, at 24 and 48 hours, only 24.0 mM arginine bicarbonate was added.

As a Non-limiting Explanation:

(1) Media containing arginine bicarbonate was able to maintain the media pH at a constant 8.3-8.6 pH level during 72 hours of incubation (see FIGS. 7 and 15). This was beneficial for the growth of *Staph. epidermidis*, which has proven herein to be a major bacterium for maintenance of a normal skin microflora and for suppressing *Staph. aureus* (MSSA or MRSA), i.e. pathogens of considerable concern. The medium containing zinc carbonate and CIL, but with no arginine bicarbonate present, had a pH between 6.1 and 6.8 (see FIGS. 7 and 15), which evidently was able to inhibit the growth of *Staph. aureus* (MSSA or MRSA) slightly to moderately (see FIGS. 6 and 14). But, it was not able to strongly inhibit *Staph. aureus* (MSSA or MRSA), in a medium containing arginine bicarbonate (see FIGS. 6 and 14 vs. 4 and 12). In contrast, *Staph. epidermidis* was quickly reduced in this medium (FIGS. 5 and 13). This would most importantly imply that a reason for this is that the alkaline pH (8.3-8.6), which promoted the growth of *Staph. epidermidis*, and its anti-*Staph. aureus* effectiveness, resulting in reduction of the growth of *Staph. aureus* (MSSA or MRSA).

(2) Evidently, as explanation, the pH is not the only factor to affect the survival of *Staph. epidermidis* and *Staph. aureus*.

Although the overall pH of the medium (zinc carbonate, arginine bicarbonate and CIL) and additional same medium or 24 mM arginine bicarbonate being added at 24 and 48 hours during 72 hours of incubation, was maintained at pH 8.3-8.6; it showed remarkably well that as more arginine bicarbonate was added to the medium, the density of *Staph. epidermidis* that was ultimately obtained was increased. Nonetheless and most importantly, this indicated that arginine bicarbonate can play a significant enhancement role in the growth of *Staph. epidermidis* and that this effect may be largely but not solely due to the elevated and sustained pH favored by the presence of arginine bicarbonate.

In contrast, *Staph. aureus* (MSSA or MRSA) incubated in the medium containing zinc carbonate, CIL and no arginine bicarbonate or in a sterile distilled water negative control (both of which show a pH in the range of 6.0-6.8) showed almost no reduction in growth after 72 hours of incubation in distilled water (see FIGS. 1, 7, 8 and 15). However, there was moderate reduction during incubation for 72 hours in a medium containing zinc carbonate, and CIL without arginine bicarbonate (see FIGS. 6 and 14). Accordingly, one can conclude that zinc carbonate is an important ingredient for suppression of *Staph. aureus* (MSSA and MRSA) growth, and plays thereof a significant inhibitory role as well.

The present invention is not limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

REFERENCES

1. Centers for Disease Control and Prevention: Public health dispatch: outbreaks of community-associated methicillin-resistant *Staphylococcus aureus* skin infections—Los Angeles County, California, 2002-2003. MMWR Morb. Mortal. Wkly. Rep., 52:88, 2003.
2. Chen, A. E., Goldstein, M., Carroll, K., Song, X., Perl, T. M., Siberry, G. K.: Evolving epidemiology of pediatric *Staphylococcus aureus* cutaneous infections in a Baltimore hospital. Pediatr. Emerg. Care, 22:717-723, 2006.
3. David, M. Z., Daum, R. S.: Community-associated methicillin-resistant *Staphylococcus aureus*: epidemiology and clinical consequences of an emerging epidemic. Clin. Microbiol. Review, 23 (3):616-87, 2010.
4. Denepitiya, L., Kleinberg, I.: A comparison of the acid-base and aciduric properties of various serotypes of the bacterium *Streptococcus* mutants associated with dental plague. Arch. Oral Biol., 29:385-393, 1984.
5. Denepitiya, L., Kleinberg, I.: A comparison of the microbial compositions of pooled human dental Plaque and salivary sediment. Arch. Oral Biol., 27:739-845, 1982.
6. Emter, R., Natsch, A.: The sequential action of a dipeptidase and a β-lyase is required for the release of the human body odorant 3-methyl-3-sulfanylhexan-1-ol from a secreted cys-gly-(s) conjugate by Corynebacteria. J. Biol. Chem., 283 (30):20645-20652, 2008.
7. Frank, D. N., Feazel, L. M., Bessesen, M. T., Price, C. S., Janoff, E. N., Pace, N. R.: The human nasal microbiota and *Staphylococcus aureus* carriage. PLOS ONE 5 (5):e10598, 2010.
8. French, G. L.: Methods for screening for methicillin-resistant *Staphylococcus aureus* carriage. Clin. Microbiol. Infect. 15 (Suppl. 7):10-16, 2009.
9. Gallo, R. L., Nakatsuji, T.: Firmocidin, an antimicrobial molecule produced by *Staphylococcus epidermidis*. U.S. Patent Application Publication 2013/0331384 A1.
10. Han, Z., Lautenbach, E., Fishman, N., Nachamkin, I.: Evaluation of mannitol salt agar, CHROMagar *Staph aureus* and CHROMagar MRSA for detection of methicillin-resistant *Staphylococcus aureus* from nasal swab specimens. J. Med. Microbiol., 56 (1):43-46, 2007.
11. Jackman, P. J. H.: Body odor—the role of skin bacteria. Sem. Dermatol., 1 (2):J43-148, 1982.
12. Kleinberg, I., Codipilly, D.: Cysteine challenge testing: a powerful tool for examining oral malodour processes and treatments in vivo. Inter. Dental J., 52:221-228, 2002.
13. Kleinberg. I., Codipilly, D.: $H_2S$ generation and Eh reduction in cysteine challenge testing as a means of determining the potential of test products and treatments for inhibiting oral malodor. J. Breath Res., 2:1-9, 2008.
14. Kleinberg, I., Codipilly, D.: Modeling of the oral malodor system and methods of analysis. Quint. Int, 30:357-396, 1999.
15. Klevens, R. M., Morrison, M. A., Nadle, J., Petit, S., Gershman, K., Petit, S., Ray, S., Harrison, L. H., Lynfield, R., Dumyati, G., Townes, J. M., Craig, A. S., Zell, E. R., Fosheim, G. E., McDougal, L. K., Carey, R. B., Fridkin, S. K.: Invasive methicillin-resistant *Staphylococcus aureus* infections in the United States, J. Am. Med. Assoc., 298: 1763-1771, 2007.

16. Leyden, J. J., McGinley, K.: Coryneform bacteria. The skin microflora and microbial skin disease. Cambridge Univ. Press, 102-141, 1992.
17. Leyden, J. J., McGonley, K. J., Hölzle. E., Labows, J. N., Kligman, A. M.: The microbiology of human axilla and its relationship to axillary odor. J. Inv. Derm., 77:413-416, 1981.
18. Mainous III, A. G., Hueston, W., Everett, C. J., Diaz, V. A.: Nasal Carriage of *Staphylococcus aureus* and Methicillin-Resistant *S aureus* in the United States 2001-2002. Ann. Fam. Med., 4 (2): 132-137, 2006.
19. Nakatsuji, T., Nam, S., Fenical, W., Gallo, R. L.: Skin commensal bacteria acts as antimicronial shield: Identification of firmocidin, a novel small-molecule antobiotoc produced by *Staphylococcus epidermidis*. J. Inv. Derm., 132:S114, 2012.
20. Nobel, W. C.: Staphylococci on the skin. The skin microflora and microbial skin disease. Cambridge Univ. Press, 135-152, 1992.
21. Pader, M.: Oral hygiene products and practice. Cosmetic science and technology series. New York, Basel: Marcel Dekker, 6:344-359, 1988.
22. Peacock, S. J., de Silva, I., Lowy, F. D.: What determines nasal carriage of *Staphylococcus aureus*? TRENDS Microbiol., 9 (12):605-610, 2001.
23. Sandham, H. J., Kleinberg, I.: Effect of glucose concentration on carbon dioxide production in a human salivary sediment system. Arch. Oral Biol., 15:1285, 1970.
24. Shehadeh, N., Kligman, A. M.,: The bacteria responsible for axillary odor II. J. Invest. Derm., 41:3, 1963.
25. Starkenmann, C., Niclass, Y., Troccaz, M., Clark, A. J.: Identification of the precursor of (S)-3 methyl-3-sulfanyl-hexan-1-ol, the sulfury malodour of human axilla sweat. Chem Biodivers., 2:705-716, 2005.
26. Taylor, D., Daulby, A., Grimshaw, S., James, G., Mercer, J., Vaziri, S.: Characterization of the microflora of the human axilla. Intern. J. Cosm. Scien., 25:137-145, 2003.
27. Troccaz, M., Starkenmann, C., Niclass, Y., Waal, Mvd., Clark, A. J.: 3 methyl-3-sulfanylhexan-1-ol, as a major descriptor for the human axilla-sweat odour profile. Chem Biodiversity, 1:1022-1035, 2004.
28. Uehara, Y., Nakama, H., Agematsu, K., Uchida, M., Kawakami, Y., Abdul Fattah, A. S. M., Maruchi, N.: Bacterial interference among nasal inhabitants: eradication of *Staphylococcus aureus* from nasal cavities by artificial implantation of *Corynebacterium* sp. J. Hosp. Infect., 44:127-133, 2000.
29. Wertheim, H. L. F., Melles, D. C., Vos, M. C., Leeumen, W. V., Belkum, A. V., Verbrugh, H. A., Nouwen, J. L.: The role of nasal carriage in *Staphylococcus aureus* infection. Lancet Infect. Dis. 5:751-62, 2005.
30. Wijeyeweera, R. L., Kleinberg, I.: Acid-base pH curves in vitro with mixtures of pure cultures of human oral microorganisms. Arch. Oral Biol., 34 (1):55-64, 1989.
31. Zeng, X. N., Leyden. J. J., Lawley, H. J., Sawano, K., Hohara, I., Preti, G.: Analysis of characteristic odors from human male axillae, J. Chem. Ecol., 17 (7): 1469-1492, 1991.

What is claimed is:

1. A method for promoting the growth of *Staphylococcus epidermidis* and inhibiting the growth of *Staphylococcus aureus* in the cutaneous microbiome, comprising topically applying to said microbiome a composition including an arginine salt; a zinc salt; and a physiologically-acceptable carrier suitable for topical application.

2. The method of claim 1, wherein the composition further includes a buffer sufficient to maintain the pH of the composition at 6.0 or greater upon topical application.

3. The method of claim 1, wherein the composition further includes a buffer sufficient to maintain the pH of the composition at 7.0 or greater upon topical application.

4. The method of claim 1, wherein the composition further includes a buffer sufficient to maintain the pH of the composition at 8.0 or greater upon topical application.

5. The method of claim 1, wherein the composition further includes a buffer sufficient to maintain the pH of the composition at 9.0 or greater upon topical application.

6. The method of claim 1, wherein the composition further includes phenylalanine.

7. The method of claim 1, wherein the composition is capable of inhibiting the growth and/or metabolism of malodor-generating microbiota present in the cutaneous regions of a subpart of the human body.

8. The method of claim 7, wherein the cutaneous regions comprise the axilla, foot-webs, and nasal atrium.

9. The method of claim 1, wherein the zinc salt is selected from the group consisting of zinc carbonate and zinc bicarbonate.

10. The method of claim 1, wherein the arginine salt is selected from the group consisting of arginine, arginine carbonate, and arginine bicarbonate.

11. The method of claim 1, wherein the zinc salt is zinc carbonate and the arginine salt is arginine bicarbonate.

12. The method of claim 1, wherein the composition includes 24 mM arginine bicarbonate and 12 mM zinc carbonate.

13. The method of claim 1, wherein the composition is provided as a topical formulation selected from the group selected from soap, spray, drop, aerosol, powder, roll-on, lotion, cream, stick, solution, sachet, colloidal suspension, film, patch, and ointment.

14. The method of claim 1, wherein the *Staphylococcus aureus* comprises MRSA.

15. The method of claim 1, wherein the *Staphylococcus aureus* comprises MSSA.

16. A method for promoting the growth of *Staphylococcus epidermidis* and inhibiting the growth of *Staphylococcus aureus* in the cutaneous microbiome, comprising topically applying to said microbiome a composition including arginine or a salt thereof; a zinc salt; and a physiologically-acceptable carrier suitable for topical application.

* * * * *